(12) United States Patent
Koentgen

(10) Patent No.: US 8,202,727 B2
(45) Date of Patent: Jun. 19, 2012

(54) SEQUENTIAL CLONING SYSTEM

(75) Inventor: Frank Koentgen, North Beach (AU)

(73) Assignee: Ozgene Pty Ltd., Bentley DC (AU)

( * ) Notice: Subject to any disclaimer, the term of this patent is extended or adjusted under 35 U.S.C. 154(b) by 961 days.

(21) Appl. No.: 11/914,519

(22) PCT Filed: May 17, 2006

(86) PCT No.: PCT/AU2006/000650
§ 371 (c)(1),
(2), (4) Date: Jun. 9, 2008

(87) PCT Pub. No.: WO2006/122354
PCT Pub. Date: Nov. 23, 2006

(65) Prior Publication Data
US 2008/0268447 A1    Oct. 30, 2008

Related U.S. Application Data

(60) Provisional application No. 60/681,461, filed on May 17, 2005.

(51) Int. Cl.
*C12N 15/00* (2006.01)
*C12N 15/63* (2006.01)
*C07H 21/02* (2006.01)

(52) U.S. Cl. .................. 435/440; 435/320.1; 536/23.1

(58) Field of Classification Search .................. None
See application file for complete search history.

(56) References Cited

U.S. PATENT DOCUMENTS

| 5,434,063 A * | 7/1995 | Lacks ........................... 435/477 |
| 2004/0126883 A1 | 7/2004 | Liu .............................. 435/455 |
| 2004/0166567 A1 | 8/2004 | Santi et al. ..................... 435/76 |
| 2009/0149406 A1 | 6/2009 | Crouzet et al. ................. 514/44 |

FOREIGN PATENT DOCUMENTS

WO      2005/103279      11/2005

\* cited by examiner

*Primary Examiner* — Michele K Joike
(74) *Attorney, Agent, or Firm* — Seed IP Law Group PLLC

(57) ABSTRACT

This invention discloses a cloning system and more particularly a system for sequentially cloning a plurality of heterologous nucleic acid sequences to assemble a chimeric construct of interest. The cloning system employs a marker sequence, which confers an identifiable characteristic on host cells in which it is contained, to chaperone individual insert nucleic acid sequences into recipient constructs that do not comprise the marker sequence but comprise other nucleic acid sequences for inclusion in the chimeric construct. Recombinant constructs into which one or more insert nucleic acid sequences have been introduced with the chaperone marker sequence are isolated by introducing recombinant constructs into host cells and identifying hosts cells with the identifiable characteristic.

17 Claims, 20 Drawing Sheets

A

B

```
                        SEQUENCE LISTING

<160> NUMBER OF SEQ ID NOS: 2

<210> SEQ ID NO 1
<211> LENGTH: 34
<212> TYPE: DNA
<213> ORGANISM: Unknown
<220> FEATURE:
<223> OTHER INFORMATION: loxP target site

<400> SEQUENCE: 1
ataacttcgt atagcataca ttatacgaag ttat                              34

<210> SEQ ID NO 2
<211> LENGTH: 48
<212> TYPE: DNA
<213> ORGANISM: Unknown
<220> FEATURE:
<223> OTHER INFORMATION: FRT target site

<400> SEQUENCE: 2
gaagttccta ttccgaagtt cctattctct agtaagtata ggaacttc               48
```

SEQUENTIAL CLONING SYSTEM

FIELD OF THE INVENTION

This invention relates generally to a cloning system and more particularly to a system for sequentially cloning a plurality of heterologous nucleic acid sequences to assemble a chimeric construct of interest. The cloning system employs a marker sequence, which confers an identifiable characteristic on host cells in which it is contained, to chaperone individual insert nucleic acid sequences into recipient constructs that do not comprise the marker sequence but comprise other nucleic acid sequences for inclusion in the chimeric construct. Recombinant constructs into which one or more insert nucleic acid sequences have been introduced with the chaperone marker sequence are isolated by introducing recombinant constructs into host cells and identifying hosts cells with the identifiable characteristic.

BACKGROUND OF THE INVENTION

Traditionally, chimeric constructs that comprise multiple unrelated or heterologous nucleic acid sequences have been constructed by inserting individual insert nucleic acid sequences into a recipient vector that comprises one or more other nucleic acid sequences required for the chimeric construct, an origin of replication and a selectable marker gene that is used to confer a trait for which one can 'select' based on resistance to a selective agent (e.g., an herbicide, antibiotic, radiation, heat, or other treatment damaging to cells without the marker gene). Typically, the insertion of an insert nucleic acid sequence into the recipient vector comprises digesting a donor vector in which the insert nucleic acid sequence is contained with one or more restriction enzymes to produce a vector backbone and a fragment with blunt or cohesive ends and comprising the insert nucleic acid sequence. This donor vector will generally comprise its own origin of replication and a selective marker gene, which may be the same as, or different than, the selectable marker gene of the recipient vector. The recipient vector is also digested with one or more restriction enzymes to produce a linearized vector with ends compatible with or matching those of the fragment. The digested donor and recipient vectors are then joined by DNA ligation or topoisomerase joining reactions and recombinant vectors containing the insert nucleic acid sequence, the other nucleic acid sequence(s) and the selectable marker gene are identified by introducing the products of the joining process into host cells (e.g., bacteria) and selecting for those that are resistant to the selective agent through the presence of the selectable marker gene corresponding to the recipient vector.

This conventional strategy has several disadvantages including (1) inefficient restriction enzyme cleavage of the vectors, (2) ligation of the fragment to the backbone of the donor vector, (3) ligation-mediated recircularization of the linearized recipient vector and/or (4) generation of linear concatemers containing multiple vectors and/or multiple inserts, which leads to a significant background of non-recombinant host cells (typically 99%) that do not contain the desired recombinant vector. As such, extensive screening of host cells is required in order to identify those with the desired recombinant vector. While this efficiency may be sufficient for simple subcloning experiments, it is unacceptable for the assembly of chimeric constructs requiring multiple heterologous nucleic acid sequences, which need to be sequentially cloned into recipient vectors to produce those constructs. Accordingly, the above conventional strategy generally requires substantial effort and time for producing a desired chimeric construct.

One traditional approach for reducing the background of non-recombinant host cells is to purify the fragment and/or the linearized vector before ligation, which requires larger amounts of vector than would otherwise be required. However, this approach requires further time-consuming steps and the efficiency of ligation of the purified product(s) is generally reduced by trace amounts of agents used for the purification.

Accordingly, there is a need for a cloning system with improved efficiency in producing recombinant vectors that comprise a plurality of unrelated nucleic acid sequences.

SUMMARY OF THE INVENTION

Accordingly, in one aspect, the present invention provides methods for sequentially cloning a plurality of nucleic acid sequences. These methods generally comprise: inserting a portable segment, which lacks an origin of replication but comprises a marker sequence, into a recipient construct that lacks the marker sequence but comprises at least one of the plurality of nucleic acid sequences (step (a)). The marker sequence confers an identifiable characteristic on host cells that contain the marker sequence. The origin of replication is typically operable in host cells used to identify recombinant constructs obtained in these methods. The insertion of the portable segment into the recipient construct results in the formation of a first recombinant construct which comprises a cassette that is portable into a recipient construct and comprises the marker sequence and the nucleic acid sequence(s). The recombinant construct is introduced into host cells (step (b)) and the hosts cells are screened for those with the identifiable characteristic to thereby identify recombinant cells that contain the recombinant construct (step (c)). The cassette is subsequently obtained from the recombinant construct corresponding to the recombinant cells (step (d)) and inserted into another recipient construct that lacks the marker sequence but comprises at least one other of the plurality of nucleic acid sequences (step (e)) to form another recombinant construct. The other recombinant construct thus formed comprises another cassette that is optionally portable into a recipient construct and comprises the cassette and the other nucleic acid sequence(s). This other recombinant construct is then introduced into host cells (step (f)) and the hosts cells are screened for those with the identifiable characteristic to thereby identify other recombinant cells that contain the other recombinant construct (step (g)). Suitably, the methods further comprise obtaining the other cassette from the other recombinant construct corresponding to the other recombinant cells (step (h)). In some embodiments, the methods further comprise repeating steps (e) to (g) and optionally (h) as necessary to assemble a chimeric construct of interest. If desired, these steps are repeated at least 1, 2, 3, 4, 5, 6, 7, 8, 9, 10 times, even at least 15, 20, 25, 30 or more times.

In some embodiments, the methods further comprise identifying recombinant host cells that display, in addition to the identifiable characteristic, a different identifiable characteristic that is conferred by another marker sequence that resides in a recipient construct. In illustrative examples, the marker sequence and the other marker sequence are selected from selectable markers and screenable markers.

Suitably, the recipient constructs are selected from vectors and nucleic acid sequences residing in the genome of a host cell.

In some embodiments, an insert cassette that is introduced into a recipient construct for the production of a respective recombinant construct is provided with another marker sequence that confers a different identifiable characteristic than the identifiable characteristic conferred by the marker sequence of the portable segment. These embodiments are particularly advantageous when the host cells into which the recombinant construct is introduced already have the identifiable characteristic.

In some embodiments, the methods further comprise excising at least a portion of the marker sequence after the assembly of the chimeric construct of interest. In illustrative examples of this type, the marker sequence is excised, in whole or in part, using a recombinase protein that recognizes target sites located within or adjacent to the marker sequence to thereby mediate the excision.

Suitably, individual nucleic acid sequences are selected from: (1) a nucleic acid sequence that is homologous with a region of a target site in the genome of a host cell; (2) a transcriptional regulatory element; (3) a translational regulatory element; (4) a sequence that comprises at least one restriction enzyme site; (5) a marker sequence; (6) a sequence that encodes a RNA molecule; (7) a sequence that encodes a polypeptide; (8) a recombination site; (9) an origin of replication; and (10) an antisense molecule.

In specific embodiments, an individual cassette represents a targeting cassette for site-specific homologous recombination at a target site in a recipient construct or in the genome of a host cell that is capable of undergoing homologous recombination.

In some embodiments, an individual cassette is amplified by nucleic acid amplification (e.g., PCR) from a donor construct and inserted into a recipient construct. Suitably, the nucleic acid amplification employs at least one primer which comprises (1) a nucleotide sequence that is complementary to a terminal portion of the cassette and (2) a site that serves to insert one end of the amplified cassette into a recipient construct. In illustrative examples of this type, the site is cleavable by a restriction enzyme.

In other embodiments, an individual cassette is physically transferred from a donor construct to a recipient construct. Suitably, the physical transfer comprises excision of the cassette from the donor construct using, for example, a restriction endonuclease, sonication, shearing or recombination.

In another aspect, the invention provides kits for cloning a nucleic acid sequence, especially for sequentially cloning a plurality of nucleic acid sequences. These kits generally comprise a plurality of donor marker constructs, each comprising a portable segment that lacks an origin of replication but comprises a marker sequence that confers an identifiable characteristic on host cells that contain the marker sequence, wherein the portable cassette of an individual donor marker construct is excisable using one or more different excising agents than the excising agent(s) used to excise the portable cassette of the other donor marker construct(s). In some embodiments, the kits comprise at least 2, 3, 4, 5, 6, 7, 8, 9, 10, even at least 15, 20, 25, 30 or more donor marker constructs. In some embodiments, the excising agents are selected from restriction endonucleases and recombinase protein, which are specific for different recognition sequences. In these embodiments, the different donor marker constructs provide a choice of excision agents to produce a portable construct that is suitable for insertion into a cloning site of a desired recipient construct.

In some embodiments, the marker sequence of individual donor mark constructs comprises or encodes a positive marker. Illustrative positive markers include selectable markers (e.g., antibiotic resistance genes) and screenable markers (e.g., a fluorescent marker gene such as EGFP or a enzymatic marker gene such as lacZ). Suitably, the marker sequence confers an identifiable characteristic (e.g., neomycin resistance, fluorescence) on both a first cell type and on a second cell type. In these instances, the first cell type is suitably selected from bacterial cells and the second cell type is suitably selected from mammalian cells. In certain non-limiting examples, the marker sequence is operably connected to a first transcriptional control sequence (e.g., EM7 promoter) that is operable in the first cell type (e.g., a bacterial cell) and to a second transcriptional control sequence (e.g., a phosphoglycerate kinase promoter) that is operable in the second cell type (e.g., a mammalian cell).

In some embodiments, the marker sequence is flanked by recombinase target sites that are recognized by a recombinase protein that mediates excision of the marker sequence from a construct in which it resides. Suitably, the target sites are selected from loxP sites and FRT sites.

In some embodiments, an individual donor marker construct comprises an origin of replication external of the portable cassette, which is suitably inactivatable (e.g., by using a cleavage agent such as a restriction endonuclease that cleaves a site in or adjacent to the origin of replication). In these embodiments, inactivation of the origin of replication on the donor marker construct decreases the incidence of obtaining host cells with the donor marker construct.

In some embodiments, the kits further comprise a first recipient construct that lacks the marker sequence but comprises at least one cloning site into which a nucleic acid sequence of interest is insertable and into which the portable segment is insertable, wherein the nucleic acid sequence and the portable segment when inserted into their corresponding cloning site(s) on the first recipient construct yield a cassette that is optionally portable into another recipient construct. In some embodiments, the kits comprise at least 1, 2, 3, 4, 5, 6, 7, 8, 9, 10, even at least 15, 20, 25, 30 or more additional recipient constructs for sequentially cloning a corresponding number of other nucleic acid sequences of interest, wherein each additional recipient construct lacks the marker sequence but comprises at least one cloning site into which another nucleic acid sequence is insertable and into which the portable cassette of the first recipient construct is insertable, wherein the other nucleic acid sequence and the cassette when inserted into their corresponding cloning site(s) on the additional recipient construct yield a further cassette that is optionally portable into another recipient construct.

In some embodiments, an individual recipient construct comprises a different cloning site than another construct of the kit, whilst in others, an individual recipient construct comprises the same cloning site as another construct of the kit. Typically, an individual recipient construct comprises an origin of replication.

In some embodiments, an individual recipient construct comprises another marker sequence that confers a different identifiable characteristic on host cells that contain that marker sequence than the identifiable characteristic conferred by the marker sequence of the donor marker construct. In illustrative examples of this type, the other marker sequence comprises a selectable marker gene (e.g., an ampicillin resistance gene) or a screenable marker gene (e.g., a fluorescent marker gene such as EGFP or a enzymatic marker gene such as lacZ).

If desired, a recipient construct or another construct of the kit can comprise a nucleic acid sequence from which a recombinase protein is expressible.

In some embodiments, the respective cloning sites of individual constructs comprise at least one restriction enzyme site.

In yet another aspect, the present invention provides kits for sequentially cloning a plurality of nucleic acid sequences. These kits generally comprise: (1) a donor marker construct comprising a portable segment that lacks an origin of replication but comprises a marker sequence that confers an identifiable characteristic on host cells that contain the marker sequence; and (2) a first recipient construct that lacks the marker sequence but comprises at least one cloning site into which a nucleic acid sequence is insertable and into which the portable segment is insertable, wherein the nucleic acid sequence and the portable segment when inserted into their corresponding cloning site(s) on the first recipient construct yield a cassette that is optionally portable into another recipient construct. In some embodiments, the kits further comprise at least one additional recipient construct that lacks the marker sequence but comprises at least one cloning site into which a further nucleic acid sequence is insertable and into which a portable cassette is insertable, wherein the further nucleic acid sequence and the portable cassette when inserted into their corresponding cloning site(s) on the additional recipient construct(s) yield another cassette that is optionally portable into a recipient construct. In illustrative examples of this type, the kits comprise at least 1, 2, 3, 4, 5, 6, 7, 8, 9, 10, even at least 15, 20, 25, 30 or more additional recipient construct(s). In some embodiments, the kits further comprise at least one other donor marker construct that comprises a portable cassette comprising the same marker sequence as the first-mentioned donor marker construct, wherein the portable cassette of the first-mentioned donor marker construct is excisable using one or more different excising agents than the excising agent(s) used to excise the portable cassette of the second-mentioned donor marker construct.

In still another aspect, the invention provides kits for cloning a nucleic acid sequence, especially for sequentially cloning a plurality of nucleic acid sequences. These kits generally comprise at least one donor marker construct, which comprises a portable segment that lacks an origin of replication but comprises a marker sequence that confers an identifiable characteristic on host cells that contain the marker sequence, wherein the portable cassette is excisable using a plurality of different excising agents such that the portable cassette when excised using at least one of the excising agents has different ends than when excised using at least one other of the excising agents. In some embodiments, the portable cassette is flanked on each side by a plurality of recognition sites, each cleavable by a different endonuclease (e.g., a plurality of different endonuclease cleavage sites). In some embodiments, the portable cassette is flanked on each side by a plurality of recombinase target sites, each recognized by a different recombinase protein. In these embodiments, an individual donor marker construct provides a choice of excising agents to provide the portable cassette with ends that are compatible with the cloning site of a recipient construct of interest. In some embodiments, the kits further comprise at least one recipient construct as broadly described above.

In still another aspect, the invention extends to the use of at least one donor marker construct as broadly described above and optionally at least one recipient construct as broadly described above in the manufacture of a kit for cloning at least one nucleic acid sequence and especially for sequentially cloning a plurality of nucleic acid sequences.

In a further aspect, the invention contemplates the use of at least one donor marker construct as broadly described above and optionally at least one recipient construct as broadly described above for sequentially cloning a plurality of nucleic acid sequences using the method broadly disclosed above.

DETAILED DESCRIPTION OF THE INVENTION

1. Definitions

Figure 1:
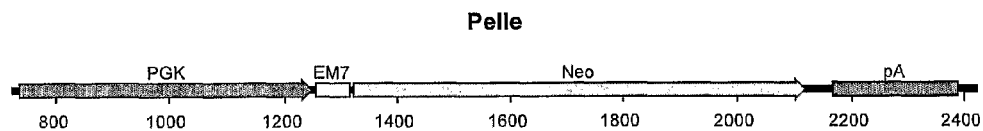
FIG. 1 is a diagrammatic representation of one embodiment of a donor marker vector that comprises an insert cassette, designated "Pelle," in accordance with the present invention.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "amplicon" refers to a target sequence for amplification, and/or the amplification products of a target sequence for amplification. In certain other embodiments an "amplicon" may include the sequence of probes or primers used in amplification.

"Amplification product" refers to a nucleic acid product generated by nucleic acid amplification techniques.

"Cells," "host cells," "transformed host cells," "regenerable host cells" and the like are terms that not only refer to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The terms "chimeric construct," "chimeric gene," "chimeric nucleic acid" and the like are used herein to refer to a gene or nucleic acid sequence or segment comprising at least two nucleic acid sequences or segments from species which do not combine those sequences or segments under natural conditions, or which sequences or segments are positioned or linked in a manner which does not normally occur in the native genome or nucleome of the untransformed host. Thus, a "chimeric gene" refers to any gene that is not a native gene, comprising regulatory and coding or non-coding sequences that are not found together in nature. In this light, a chimeric gene may comprise regulatory sequences and coding or non-coding sequences that are derived from different sources, or regulatory sequences and coding or non-coding sequences derived from the same source, but arranged in a manner different than that found in nature.

By "coding sequence" is meant any nucleic acid sequence that contributes to the code for the polypeptide product of a gene.

Throughout this specification, unless the context requires otherwise, the words "comprise," "comprises" and "comprising" will be understood to imply the inclusion of a stated step or element or group of steps or elements but not the exclusion of any other step or element or group of steps or elements.

"Constitutive promoter" refers to a promoter that directs expression of an operably linked transcribable sequence in many or all tissues of an organism.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

The term "endogenous" refers to a gene or nucleic acid sequence or segment that is normally found in a host organism.

The term "endogenous genomic nucleic acid sequence" is defined herein as a nucleotide sequence that is normally present within the genome of a cell. As disclosed herein, endogenous genomic nucleic acid sequences are capable of undergoing site-specific homologous recombination with sequences of a targeting construct of the invention and, therefore, can be utilised as a target for modification by the disclosed targeting constructs. Sequences included within this definition can represent any coding or non-coding regions of specific genes present within the cellular genome. Such genes include transcribable nucleic acid sequences as defined herein. Endogenous genomic nucleic acid sequences can also represent regulatory elements such as promoters, enhancers or repressor elements. The organization of the endogenous genomic target nucleic acid sequence is generally similar to specific sequences present within the targeting construct. That is, it contains sequences which are substantially homologous to sequences present within the targeting construct that allow for site-specific homologous recombination to occur.

The term "expression" with respect to a gene sequence refers to transcription of the gene and, as appropriate, translation of the resulting mRNA transcript to a protein. Thus, as will be clear from the context, expression of a coding sequence results from transcription and translation of the coding sequence. Conversely, expression of a non-coding sequence results from the transcription of the non-coding sequence.

The terms "flanked by," "flanking" and the like as they apply to relationships between two or more nucleotide sequences in targeting constructs of the invention do not require one of these nucleotide sequences to be located directly adjacent to another nucleotide sequence. For example, three reference nucleotide sequences (A, B and C) may be flanked by recombination target site sequences, or recombination target sites sequences may be flanking those reference sequences, even though reference sequence B is not directly adjacent to these sites. Accordingly, the term "flanked by" is equivalent to being "in between" the recombination sites and the term "flanking" is equivalent to the recombination sites being upstream or downstream of a reference sequence.

As used herein, the terms "function" or "functional activity" refer to a biological, enzymatic, or therapeutic function.

The term "gene" as used herein refers to any and all discrete coding regions of a host genome, or regions that code for a functional RNA only (e.g., tRNA, rRNA, regulatory RNAs such as ribozymes, post-transcription gene silencing—(PTGS) associated RNAs etc) as well as associated non-coding regions and optionally regulatory regions. In certain embodiments, the term "gene" includes within its scope the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The gene sequences may be cDNA or genomic DNA or a fragment thereof. The gene may be introduced into an appropriate vector for extrachromosomal maintenance or for integration into the host.

The term "host" refers to any organism, or cell thereof, whether eukaryotic or prokaryotic into which a recombinant construct can be stably or transiently introduced.

By "isolated" is meant material that is substantially or essentially free from components that normally accompany it in its native state. For example, an "isolated polynucleotide", as used herein, refers to a polynucleotide, which has been purified from the sequences which flank it in a naturally occurring state, e.g., a DNA fragment which has been removed from the sequences which are normally adjacent to the fragment.

As used herein, the term "join" or "joining" refers to both covalent and non-covalent attachment of one nucleic acid to another, or one end of a nucleic acid to another end of a nucleic acid. "Covalent" joining refers to the attachment of one end of a nucleic acid strand to another end of a nucleic acid strand via a phosphate bond or to attachment of one end of a double-stranded nucleic acid to another double-stranded end via phosphate bonding on one or both strands. "Non-covalent" joining refers to attachment of one end of a nucleic acid to another end via annealing of a single-stranded regions to each other; that is, no phosphate bond is generated in this embodiment.

"Ligate" or "ligated" refers to the covalent joining of two ends of one or more nucleic acid molecules.

The term "knock-in" generally refers to a heterologous or foreign gene or part thereof that has been inserted into a genome through homologous recombination. The knock-in gene or gene part may be a mutant form of a gene or gene part that replaces the endogenous, wild-type gene or gene part. Such mutations include insertions of heterologous sequences, deletions, point mutations, frameshift mutations and any other mutations that may prevent, disrupt or alter normal gene expression. Thus, a "knock-in" animal, as used herein, refers to a genetically modified animal in which a specific gene or part thereof is replaced by a foreign gene or DNA sequence. A "conditional knock-in" refers to a heterologous or foreign gene or part thereof that has been inserted into a genome through homologous recombination and that is expressed at a designated developmental stage or under particular environmental conditions. A "conditional knock-in vector" is a vector including a heterologous or foreign gene or part thereof that can be inserted into a genome through homologous recombination and that can be expressed at a designated developmental stage or under particular environmental conditions.

By "knock-out" is meant the inactivation or loss-of-function of a gene, which decreases, abrogates or otherwise inhibits the level or functional activity of an expression product of that gene. A "knock-out" animal refers to a genetically modified animal in which a gene is inactivated or loses function. A "conditional knock-out" refers to a gene that is inactivated or loses function under specific conditions, such as a gene that is inactivated or loses function in a tissue-specific or a temporal-specific pattern. A "conditional knock-out vector" is a vector including a gene that can be inactivated or whose function can be lost under specific conditions.

The term "mammal" is used herein in its broadest sense and includes rodents, primates, ovines, bovines, ruminants, lagomorphs, porcine, caprices, equines, canines, and felines. Preferred non-human mammals are selected from the order Rodentia that includes murines (e.g., rats and mice), most preferably mice.

By "marker gene" is meant a gene that imparts a distinct phenotype to cells expressing the marker gene and thus allows such transformed cells to be distinguished from cells that do not have the marker. A selectable marker gene confers a trait for which one can 'select' based on resistance to a selective agent (e.g., an herbicide, antibiotic, radiation, heat, or other treatment damaging to untransformed cells). A screenable marker gene (or reporter gene) confers a trait that one can identify through observation or testing, i.e., by 'screening' (e.g. β-glucuronidase, luciferase, green fluorescent protein or other activity not present in untransformed cells).

The term "non-coding sequence" refers to any nucleic acid sequence that does not contribute to the code for the polypeptide product of a gene.

The term "5' non-coding region" is used herein in its broadest context to include all nucleotide sequences which are derived from the upstream region of an expressible gene, other than those sequences which encode amino acid residues which comprise the polypeptide product of the gene, wherein 5' non-coding region confers or activates or otherwise facilitates, at least in part, expression of the gene.

By "nucleome" is meant the total nucleic acid complement and includes the genome, extrachromosomal nucleic acid molecules and all RNA molecules such as mRNA, heterogenous nuclear RNA (hnRNA), small nuclear RNA (snRNA), small nucleolar RNA (snoRNA), small cytoplasmic RNA (scRNA), ribosomal RNA (rRNA), translational control RNA (tcRNA), transfer RNA (tRNA), eRNA, messenger-RNA-interfering complementary RNA (micRNA) or interference RNA (iRNA), chloroplast or plastid RNA (cpRNA) and mitochondrial RNA (mtRNA).

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

The terms "operably connected," "operably linked," "in operable linkage," "in operable connection" and the like are used herein to refer to the placement of a transcribable sequence under the regulatory control of a promoter, which controls the transcription and optionally translation of the sequence. In the construction of heterologous promoter/transcribable sequence combinations, it is generally desirable to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the desirable positioning of a regulatory sequence element with respect to a heterologous gene to be placed under its control is defined by the positioning of the element in its natural setting; i.e. the genes from which it is derived.

The term "origin of replication" refers to a nucleic acid sequence that confers functional replication capabilities in a host cell. In the context of the phrase "a portable segment that lacks an origin of replication" and the like, this term shall be construed as encompassing origins of replication that are not functional in a host cell into which the portable cassette is to be introduced but not excluding origins of replication that are functional in other host cells.

The term "polynucleotide" or "nucleic acid" as used herein designates mRNA, RNA, cRNA, cDNA or DNA. The term typically refers to oligonucleotides greater than 30 nucleotides in length.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

By "primer" is meant an oligonucleotide which, when paired with a strand of DNA, is capable of initiating the synthesis of a primer extension product in the presence of a suitable polymerizing agent. The primer is typically single-stranded for maximum efficiency in amplification but may alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridize and serve as a site for the initiation of synthesis. By "substantially complementary," it is meant that the primer is sufficiently complementary to hybridize with a target nucleotide sequence. Suitably, the primer contains no mismatches with the template to which it is designed to hybridize but this is not essential. For example, non-complementary nucleotides may be attached to the 5' end of the primer, with the remainder of the primer sequence being complementary to the template. Alternatively, non-complementary nucleotides or a stretch of non-complementary nucleotides can be interspersed into a primer, provided that the primer sequence has sufficient complementarity with the sequence of the template to hybridize therewith and thereby form a template for synthesis of the extension product of the primer.

By "promoter" is meant a region of DNA, which controls at least in part the initiation and level of transcription. Reference herein to a "promoter" is to be taken in its broadest context and includes the transcriptional regulatory sequences of a classical genomic gene, including a TATA box and CCAAT box sequences, as well as additional regulatory elements (i.e., activating sequences, enhancers and silencers) that alter gene expression in response to developmental and/or environmental stimuli, or in a tissue-specific or cell-type-specific manner. A promoter is usually, but not necessarily, positioned upstream or 5', of a transcribable sequence (e.g., a coding sequence or a sequence encoding a functional RNA), the expression of which it regulates. Furthermore, the regulatory elements comprising a promoter are usually positioned within 2 kb of the start site of transcription of the gene. Promoters according to the invention may contain additional specific regulatory elements, located more distal to the start site to further enhance expression in a cell, and/or to alter the timing or inducibility of expression of a structural gene to which it is operably connected. The term "promoter" also includes within its scope inducible, repressible and constitutive promoters as well as minimal promoters. Minimal promoters typically refer to minimal expression control elements that are capable of initiating transcription of a selected DNA sequence to which they are operably linked. In some examples, a minimal promoter is not capable of initiating transcription in the absence of additional regulatory elements (e.g., enhancers or other cis-acting regulatory elements) above basal levels. A minimal promoter frequently consists of a TATA box or TATA-like box. Numerous minimal promoter sequences are known in the literature. For example, minimal promoters may be selected from a wide variety of known sequences, including promoter regions from fos, CMV, SV40 and IL-2, among many others. Illustrative examples are provided which use a minimal CMV promoter or a minimal IL2 gene promoter (−72 to +45 with respect to the start site; Siebenlist, 1986).

By "recombinase target site" (RTS) is meant a nucleic acid sequence which is by a recombinase for the excision of the intervening sequence. It is to be understood that two RTSs are required for excision. Thus, when a Cre recombinase is used, each RTS comprises a loxP site; when loxP sites are used, the corresponding recombinase is the Cre recombinase. That is, the recombinase must correspond to or recognise the RTSs. When the FLP recombinase is used, each RTS comprises a FLP recombination target site (FRT); when FRT sites are used, the corresponding recombinase is the FLP recombinase.

The term "regulatable promoter" refers to promoters that direct gene expression not constitutively, but in a temporally- and/or spatially-regulated manner, and include both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in host cells are constantly being discovered. Since in most cases the exact boundaries of regulatory sequences have not been completely defined, nucleic acid fragments of different lengths may have identical promoter activity.

"Regulatory sequences" or "regulatory elements" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences.

The term "site-specific homologous recombination" refers to strand exchange crossover events between nucleic acid sequences substantially similar in nucleotide composition. These crossover events can take place between sequences contained in the targeting construct of the invention and endogenous genomic nucleic acid sequences. In addition, it is possible that more than one site-specific homologous recombination event can occur, which would result in a replacement event in which nucleic acid sequences contained within the targeting construct have replaced specific sequences present within the endogenous genomic sequences.

The term "substantially non-homologous" or "substantially not homologous" refers to segments of the targeting construct, which do not contain nucleotide sequences similar enough to target genomic sequences to allow for the process of site-specific homologous recombination to occur. Dissimilar sequences of this capacity fail to undergo site-specific homologous recombination with target genomic sequences due to the mismatch of base pair composition between the two sequences.

The term "transcribable nucleic acid sequence" or "transcribed nucleic acid sequence" excludes the non-transcribed regulatory sequence that drives transcription. Depending on the aspect of the invention, the transcribable sequence may be derived in whole or in part from any source known to the art, including a plant, a fungus, an animal, a bacterial genome or episome, eukaryotic, nuclear or plasmid DNA, cDNA, viral DNA or chemically synthesised DNA. A transcribable sequence may contain one or more modifications in either the coding or the untranslated regions, which could affect the biological activity or the chemical structure of the expression product, the rate of expression or the manner of expression control. Such modifications include, but are not limited to, insertions, deletions and substitutions of one or more nucleotides. The transcribable sequence may contain an uninterrupted coding sequence or it may include one or more introns, bound by the appropriate splice junctions. The transcribable sequence may also encode a fusion protein. In other embodiments, the transcribable sequence comprises non-coding regions only.

The term "transformation" means alteration of the genotype of a host by the introduction of an expression system according to the invention.

The term "transgene" is used herein to describe genetic material that has been or is about to be artificially introduced into the nucleome, especially the genome, of a host and that is transmitted to the progeny of the host. The transgene is used to transform a host cell, meaning that a permanent or transient genetic change, especially a permanent genetic change, is induced in a host cell following incorporation of one or more nucleic acid components of the expression system as defined herein.

As used herein, the term "transgenic" or "transformed" with respect to a host cell, host part, host tissue or host means a host cell, host part, host tissue or host which comprises an targeting cassette or derivative thereof but not the modulator gene of the invention, which has been introduced into the nucleome, especially the genome, of a host cell, host part, host tissue or host.

By "vector" is meant a nucleic acid molecule, suitably a DNA molecule derived, for example, from a plasmid, bacteriophage, or plant virus, into which a nucleic acid sequence may be inserted or cloned. A vector typically contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a marker such as an antibiotic resistance gene that can be used for identification of suitable transformants. Examples of such resistance genes are well known to those of skill in the art.

2. Abbreviations

The following abbreviations are used throughout the application:

nt=nucleotide
nts=nucleotides
aa=amino acid(s)
kb=kilobase(s) or kilobase pair(s)
kDa=kilodalton(s)
d=day
h=hour
s=seconds 3. System for Sequentially Cloning a Plurality of Nucleic Acid Sequences The present invention is predicated in part on a novel strategy for sequentially cloning a plurality of heterologous nucleic acid sequences to assemble a chimeric construct of interest. This strategy employs a marker sequence, which confers an identifiable characteristic on host cells that contain that sequence, to chaperone at least one of the heterologous nucleic acid sequences into a recipient construct that does not comprise the marker sequence but comprises one or more other heterologous nucleic acid sequences for assembly of the chimeric construct. Generally, the chaperoned nucleic acid sequences and the marker sequence are introduced into the recipient construct in the form of a cassette that lacks an origin of replication so that the cassette is substantially unable to autonomously replicate by itself in the host cells used for recombinant construct identification. The recombinant construct formed by the introduction of the cassette into the recipient construct comprises the chaperoned nucleic acid sequence(s), the other nucleic acid sequence(s) and the marker sequence, all of which form at least a portion of another cassette that is substantially unable to autonomously replicate by itself and is optionally portable into a recipient construct that comprises one or more additional heterologous nucleic acid sequences. The presence of the marker sequence in the other cassette facilitates the identification of recombinant host cells that contain the recombinant construct, which generally comprises introducing the recombinant construct into host cells that do not display the identifiable characteristic and identifying recombinant host cells that display the identifiable characteristic. If desired, the identification of recombinant host cells can be confirmed by screening for host cells that also display another identifiable characteristic that is conferred by a marker sequence residing in the recipient construct.

If one or more additional nucleic acid sequences are required to assemble the chimeric construct of interest, then the other cassette is introduced into another recipient construct that comprises the additional nucleic acid sequence(s) to thereby form another recombinant construct in which the other cassette and the additional nucleic acid sequence(s) form at least a portion of a further cassette that is substantially unable to autonomously replicate by itself and is optionally portable into a recipient construct that comprises one or more further heterologous nucleic acid sequences. The presence of the marker sequence in the further cassette facilitates the identification of recombinant host cells that contain the other recombinant construct, using similar steps as those discussed for identifying recombinant cells containing the first-mentioned recombinant construct. Optionally, the identification of recombinant host cells can be confirmed by screening for host cells that also display a different identifiable characteristic that is conferred by another marker sequence residing in the other recipient construct.

The above procedure is repeated as necessary for any further nucleic acid sequences that are required for assembly of the chimeric construct of interest until that construct is assembled. Typically, the procedure is repeated at least 1, 2, 3, 4, 5, 6, 7, 8, 9, 10 times, even at least 11, 12, 13, 14, 15, 16, 17, 18, 19, 20, 21, 22, 23, 24, 25, 26, 27, 28, 29, 30 or more times.

Thus, unlike conventional cloning strategies that rely on a marker which resides in a recipient construct for selecting and screening host cells that contain a recombinant construct, the present strategy employs a marker sequence that is present in a portable segment or insert cassette but absent in recipient constructs to chaperone a heterologous nucleic acid sequence into one recipient construct and then sequentially into at least one other, whereby additional heterologous nucleic acid sequences are chaperoned by the marker sequence into each successive recipient construct. The incidence of non-recombinant constructs is markedly reduced using this strategy because recombinant constructs are identified on the basis of an identifying characteristic that is conferred by a marker sequence that is present in an individual insert cassette rather than a marker sequence that is present in a recipient construct, thereby substantially reducing the incidence of host cells with recipient constructs alone. Additionally, individual insert cassettes lack an origin of replication and are thereby substantially incapable of replicating autonomously. In some embodiments, a donor construct from which a marker sequence or an individual insert cassette is obtained, comprises an inactivatable origin of replication external of the portable cassette. Inactivation of the origin of replication may be achieved by any suitable means (e.g., by using a cleavage agent such as a restriction endonuclease that cleaves a site in or adjacent to the origin of replication). In these embodiments, inactivation of the origin of replication on the donor construct decreases the incidence of obtaining host cells with the donor marker construct.

In some embodiments, a marker sequence contained in an insert cassette and a marker sequence contained in a recipient construct are used to confer two different identifiable characteristics on host cells. In these embodiments, an even greater enrichment is obtained for host cells containing the desired recombinant construct because any host cells containing insert alone or recipient construct alone would not display both identifiable characteristics. The enrichment thus achieved effectively reduces or avoids the need to purify the insert cassette and recipient construct backbone before ligation-mediated joining or topoisomerase-mediated joining of the cassette and backbone, which can usually take between 1 and 2 days to carry out, as required by conventional cloning strategies. Accordingly, these embodiments of the present invention provide significant savings in both time and resources for each cloning step, so that the greater the number of individual cloning steps required to assemble a chimeric construct of interest, the greater the saving will be (e.g., up to 2-3 weeks for chimeric constructs requiring 4-6 cloning steps for assembly).

Individual recipient constructs may be selected from vectors that are compatible with a host cell in which the recombinant constructs would be produced. Alternatively, they may define nucleic acid sequences contained in the genome of a host cell.

Typically, each cloning step involves introducing an insert cassette, comprising the marker sequence and optionally one or more heterologous nucleic acid sequences, into a site on a recipient construct. Generally, the insert cassette will lack an origin of replication so that it is substantially incapable of replicating autonomously in a host cell. Alternatively, if the insert cassette comprises an origin of replication, then it is rendered substantially non-functional by recombinant or mutagenic techniques or any other technique suitable for that purpose as known to persons skilled in the art.

In some embodiments, the site on the recipient construct, into which the insert cassette is inserted, comprises at least one restriction enzyme site that is cleavable by a corresponding restriction enzyme to provide the recipient construct with at least one ligation substrate site, which typically defines a blunt or cohesive end of a linearized recipient construct that is substantially complementary to or compatible with one or both ends of the insert cassette. Usually, the restriction enzyme site (s) used to cleave the recipient construct is (are) not present in the construct backbone that is adapted to receive the insert cassette. In these embodiments, the insert cassette is also provided with ends complementary with or matching those of the recipient construct to enable ligation of the insert cassette into that construct. The insert cassette is obtained, for example, by cleaving a donor construct that comprises the insert cassette with one or more restriction enzymes to provide the matching ends. Generally, the restriction enzyme site(s) used to cleave the donor construct are not present in the insert cassette itself.

Alternatively, the insert cassette is obtained by amplifying the insert cassette with specific primers in a template dependent nucleic acid amplification. Several template dependent nucleic acid amplification processes are available for amplification of the insert cassette. For example, the polymerase chain reaction method (PCR), as described by Mullis et al., (see U.S. Pat. Nos. 4,683,195, 4,683,202, and 4,800,159; and European Patent Application Nos. 86302298.4, 86302299.2, and 87300203.4, and Methods in Enzymology, Volume 155, 1987, pp. 335-350), is one of the most prominent methods.

PCR involves the use of a pair of specific oligonucleotides as primers for the two complementary strands of the double-stranded DNA containing the target sequence. The primers are chosen to hybridize at the ends of each of the complementary target strands, 3' of the target sequence. Template-dependent DNA synthesis, on each strand, can then be catalyzed using a thermostable DNA polymerase in the presence of the appropriate reagents. A thermal cycling process is required to form specific hybrids prior to synthesis and then to denature the double stranded nucleic acid formed by synthesis. Repeating the cycling process geometrically amplifies the target sequence.

A PCR method employing a reverse transcription step is also used with an RNA target using RNA-dependent DNA polymerase to create a DNA template. The PCR method has been coupled to RNA transcription by incorporating a promoter sequence into one of the primers used in the PCR reaction and then, after amplification by the PCR method, using the double-stranded DNA as a template for the transcription of single-stranded RNA. (see, e.g., Murakawa et al., DNA 7:287-295 (1988)).

There are, however, several non-PCR-based amplification methods that can be used for amplifying the insert cassette. One type of non-PCR-based amplification method includes multiple cycles of DNA-dependent RNA polymerase-driven RNA transcription amplification or RNA-directed DNA synthesis and transcription to amplify DNA or RNA targets (see, e.g., Burg et al., WO 89/01050; Gingeras et al., WO 88/10315; Kacian and Fultz, EPO Application No. 89313154; Davey and Malek, EPO Application No. 88113948.9; Malek et al., W091/02818 and U.S. Pat. No. 5,130,238; Davey et al., U.S. Pat. Nos. 5,409,818; 5,466,586; 5,554,517 and 6,063,603; Eberwine et al., U.S. Pat. No. 5,514,545; Lin et al., U.S. Pat. No. 6,197,554; and Kacian et al., U.S. Pat. No. 5,888,779).

Another type of amplification method uses a ligase chain reaction (LCR), as described, for example, in European Patent Publication No. 320,308. This method requires at least four separate oligonucleotides, two of which hybridize to the same nucleic acid template so their respective 3' and 5' ends are juxtaposed for ligation. The hybridized oligonucleotides are then ligated, forming a complementary strand on the nucleic acid template. The double-stranded nucleic acid is then denatured, and the third and fourth oligonucleotides are hybridized with the first and second oligonucleotides that were joined together. The third and fourth oligonucleotides are then ligated together. Amplification is achieved by further cycles of hybridization, ligation, and denaturation.

Yet another amplification method is the Qβ replicase (Qβ) method, as described, for example, in PCT Publication Ser. No. 87/06270 and U.S. Pat. No. 4,786,600, which uses a specific RNA probe which is capable of specific transcription by a replicase enzyme. The method requires the design and synthesis of RNA probes with replicase initiation sites.

Alternatively, palindromic probes can be used as described, for example, in EPO Publication Nos. 0427073A and 0427074A to form a hairpin with a nucleic acid target sequence. The probe contains a functional promoter located in the hairpin region from which RNA transcripts are produced.

There are also several versions of a strand displacement amplification method that uses one strand of DNA to displace same strand DNA sequences hybridized to their complementary DNA sequences to generate many copies of the target DNA sequences under isothermal conditions.

Walker et al., Proc. Nati. Acad. Sci. U.S.A., 89:392-396 (January 1992), Walker et al., Nucl. Acids Res. 20:1691-1696 (1992), European Patent Application No. EP 0 497272, and European Patent Application No. EP 0 500 224, describe an oligonucleotide-driven amplification method using a restriction endonuclease. The restriction endonuclease nicks the DNA/DNA complex to enable an extension reaction and, therefore, amplification.

Becker et al., EPO Application No. 88306717.5, describe an amplification method in which a primer is hybridized to a nucleic acid sequence and the resulting duplex cleaved prior to the extension reaction and amplification.

Dattagupta et al. describe another version of the strand displacement amplification method, which employs a nucleic acid polymerase lacking 5' exonuclease activity and a set of oligonucleotide primers to carry out isothermal amplification without requiring exonuclease activity or restriction endonuclease activity (U.S. Pat. No. 6,214,587).

Still another amplification method that can be used in an amplification of the insert cassette is rolling circle amplification. This method involves insertion of a nucleic acid molecule of interest in a linear vector to form a circular vector where one strand is continuous and the other strand is discontinuous. The continuous strand of the circular vector is then amplified by rolling circle replication, amplifying the inserted nucleic acid molecule in the process. The amplification is rapid and efficient since it involves a single, isothermal reaction that replicates the vector sequences exponentially (U.S. Pat. No. 6,287,824 to Lizardi).

A related amplification method using a similar approach is termed ramification extension amplification (RAM), U.S. Pat. No. 5,942,391 to Zhang et al. The RAM method involves hybridizing a target nucleic acid to several non-overlapping oligonucleotide probes that hybridize to adjacent regions in the target nucleic acid, the probes being referred to as capture/amplification probes and amplification probes, respectively, in the presence of paramagnetic beads coated with a ligand-binding moiety. Through the binding of a ligand attached to one end of the capture/amplification probe and the specific hybridization of portions of the probes to adjacent sequences in the target nucleic acid, a complex comprising the target nucleic acid, the probes and the paramagnetic beads is formed. The probes may then ligate together to form a contiguous ligated amplification sequence bound to the beads, which complex may be denatured to remove the target nucleic acid and unligated probes.

In some embodiments, at least one primer or other oligonucleotide, which is used to amplify the insert cassette in a nucleic acid amplification reaction, comprises a restriction enzyme site that is cleavable by a corresponding restriction enzyme to provide the amplified insert cassette or amplicon with at least one ligation substrate site, which typically comprises a blunt or cohesive end that matches an end of the recipient construct. Typically, the restriction enzyme site of the primer is located upstream (5') of a targeting sequence that is substantially complementary to a target sequence in the insert cassette.

In other embodiments, the at least one primer or other oligonucleotide comprises a topoisomerase recognition site (e.g., a topoisomerase I recognition site) so that the amplified insert cassette comprises a topoisomerase recognition site at one end of the insert. The recognition site is reacted with a topoisomerase enzyme to produce a covalent intermediate comprising the topoisomerase and the amplified insert cassette and the covalent intermediate is reacted with a recipient construct that is a substrate for topoisomerase-mediated joining with the covalent intermediate. In other configurations, the recipient construct can be equipped with a topoisomerase recognition sequence and reacted with the insert cassette. In yet other configurations, both the recipient construct and the insert cassette may be equipped with topoisomerase recognition sites. Methods of cloning using topoisomerase are commercially available from Invitrogen Corporation, Carlsbad, Calif. Methods employing both recombinational cloning and topoisomerase-mediated cloning in conjunction have also been described (see, e.g., WO 02/46372).

The insert cassette and recipient construct with compatible ligation substrate sites or compatible topoisomerase substrate sites are then subjected to ligation or topoisomerase-mediated joining and the products of the joining are introduced into host cells. The host cells are then screened for the presence of the identifiable characteristic conferred by the portable marker sequence and optionally for the presence the identifiable characteristic conferred by a recipient construct marker sequence to thereby identify host cells containing the recombinant construct.

In other embodiments, the site into which the insert cassette is inserted comprises a target site that includes target sequences that are sufficiently homologous with portions of the insert cassette, which flank the marker sequence and permit host cell-mediated homologous recombination between the insert cassette and the target site. The flanking portions of the insert cassette, which are substantially homologous to target sequences in the target site, are crucial parameters that must be correctly addressed for successful targeting. In general, one region of homology can be as small as 25 bp (Ayares et al. 1986, *Genetics* 83:5199), although it is recommended that significantly larger regions of homology be utilized, as will be appreciated artisans of ordinary skill. The flanking portions may comprise any sequence that is homologous with the target site and may comprise non-coding or coding nucleic acid sequences.

Desirably, the flanking portions display significantly high sequence identity or homology to cellular endogenous target genomic sequences. High homology allows for efficient base pairing during the crossover and strand exchange process of site-specific homologous recombination. Any mismatch base pairing between the flanking portions and target site disfavors the recombination reaction. It is desirable, for example, that the flanking portions are 100% homologous (i.e., isogenic) to the target site, less desirable that they are 80% homologous and even less desirable that they are 50% homologous. When using non-isogenic flanking portions, these portions are usually at least about 1,500 nts, 2,000 nts, 2,500 nts, 3,000 nts or more in length. Generally, the insert cassette and recipient construct sequences are substantially non-homologous to host cell endogenous genomic sequences and therefore do not undergo site-specific recombination with those sequences.

Typically, in the recombination embodiments described above, the insert cassette is introduced into a host cell comprising the recipient construct and permitting homologous recombination between the insert cassette and the target site in the recipient construct. Suitably, the recipient construct in these embodiments forms part of the nucleome of the host cells and may comprise, for example, an autonomously replicating extrachromosomal vector in the host cell or the genome of the host cell. After allowing sufficient time for homologous recombination to occur, the host cells are screened for the presence of the identifiable characteristic conferred by the portable marker sequence and optionally for the presence the identifiable characteristic conferred by a recipient construct marker sequence to thereby identify host cells containing the recombinant construct.

The marker sequence of an insert cassette and optionally of a recipient construct may comprise any sequence that confers an identifiable characteristic. The identifiable characteristic may simply reside in the detectability of the marker sequence per se, e.g., by a nucleic acid analysis technique, such as but not limited to restriction enzyme analysis, sequence analysis, Southern blotting, northern blotting, and polymerase chain reaction (PCR). In other embodiments, the identifiable characteristic resides in an activity or physical feature of an expression product of the marker sequence. In these embodiments, the marker sequence defines a marker gene that comprises a promoter that is operably connected to a nucleotide sequence that encodes a marker (e.g., transcript or protein), wherein the marker confers a phenotype on a cell in which it is expressed to facilitate the identification and/or selection of cells that contain and express the marker gene. Illustrative markers of this type include signal-producing proteins, epitopes, fluorescent or enzymatic markers, or inhibitors of cellular function. For instance, selectable markers can be selected from marker enzymes such as β-galactosidase, or β-lactamase, reporter or signal-producing proteins such as luciferase or GFP, ribozymes, RNA interference (RNAi) molecules, conditional transcriptional regulators such as a Tet repressor or measurement proteins such as proteins that signals cell state, e.g., a protein that signals intracellular membrane voltage. In certain instances, the markers are "secretable markers" whose secretion can be detected as a means of identifying or selecting for transformed cells. Examples include secretable antigens that can be identified by antigen-binding molecules (e.g., antibodies), or secretable enzymes that can be detected by their catalytic activity. Secretable proteins include, but are not restricted to, proteins that are inserted or trapped in the cell wall (e.g., proteins that include a leader sequence such as that found in the expression unit of extensin or tobacco PR-S); small, diffusible proteins detectable, e.g. by ELISA; and small active enzymes detectable in extracellular solution (e.g., α-amylase, β-lactamase, phosphinothricin acetyltransferase).

In some embodiments, the marker is an antigen (e.g., protein-containing epitopes), which is generally selected from proteins and glycoproteins or portions thereof that are not normally detected in the host cell by immunohistological techniques. For example, the antigen can be CD4 (a protein normally expressed in the immune system) and be expressed and detected in non-immune cells (e.g., ES cells or plant cells).

In other embodiments, the marker is a selectable marker that confers resistance or tolerance to a selection agent. Illustrative examples of this type (and their selection agents) include, but are not restricted to, kanamycin kinase, neomycin phosphotransferase and aminoglycoside phosphotransferase (kanamycin, paromomycin, G418 and the like), puromycin N-acetyl transferase and puromycin resistance protein (puromycin), hygromycin phosphotransferase (hygromycin), bleomycin resistance protein (bleomycin), phleomycin binding protein (phleomycin), blasticidin deaminase (blasticidin), β-lactamase (ampicillin), tetracycline resistance protein (tetracycline), guanine phosphoribosyltransferase (xanthine), glutamine synthetase and the acetyl transferase gene from *Streptomyces viridochromogenes* described in EP-A 275 957 (phosphinothricin), hypoxanthine guanine phosphoribosyl transferase (hypoxanthine), chloramphenicol acetyltransferase (chloramphenicol), glutathione-S-transferase (glutathione), histidinol dehydrogenase (histidinol) 5-enolshikimate-3-phosphate synthase (EPSPS) (N-phosphonomethylglycine), barstar (bialaphos), a nitrilase such as Bxn from *Klebsiella ozaenae* (bromoxynil), dihydrofolate reductase (methotrexate), mutant acetolactate synthase (ALS) as described in EP-A-154 204 (imidazolinone, sulfonylurea or other ALS-inhibiting chemicals), mutated anthranilate synthase (5-methyl tryptophan), and dalapon dehalogenase gene (2,2-dichloropropionic acid) and their biologically active fragments, variants and derivatives. In specific embodiments, the selectable marker confers resistance or tolerance to a selection agent on at least two different host cells. Suitably, these host cells are from different organisms or define different organisms, e.g., bacteria, yeast, plants, insects, avians, reptiles and mammals. For example, kanamycin/neomycin resistance can be conferred on both bacterial cells and mammalian cells.

In still other embodiments, the marker is a screenable marker. Desirable screenable markers include, but are not limited to, β-glucuronidase (GUS) enzyme for which various chromogenic substrates are known; horseradish peroxidase for which various chromogenic substrates are known; β-galactosidase for which chromogenic substrates are known; human placental alkaline phosphatase and alkaline phosphatase for which various chromogenic substrates are known; aequorin which may be employed in calcium-sensitive bioluminescence detection; β-lactamase which encodes an enzyme for which various chromogenic substrates are known (e.g., PADAC, a chromogenic cephalosporin); an R-locus gene product that regulates the production of anthocyanin pigments (red colour) in plant tissues (Dellaporta et al., 1988, in Chromosome Structure and Function, pp. 263-282); α-amylase (Ikuta et al., 1990, Biotech., 8:241); tyrosinase (Katz et al., 1983, J. Gen. Microbiol., 129:2703) which oxidises tyrosine to dopa and dopaquinone which in turn condenses to form the easily detectable compound melanin; or a xylose transporter (Zukowsky et al., 1983, Proc. Natl. Acad. Sci. USA 80:1101), which encodes a catechol dioxygenase that can convert chromogenic catechols. Alternatively, the screenable marker may be selected from fluorescent proteins such as green fluorescent protein (GFP), including particular mutant or engineered forms of GFP such as BFP, CFP, YFP (Aurora Biosciences) (see, e.g., Tsien et al., U.S. Pat. No. 6,124,128), and enhanced GFP (EGFP), as well as DsRed (Clontech), blue, cyan, green, yellow or red fluorescent proteins (Clontech, Feng et al., 2000, Neuron, 28:41-51), rapidly degrading GFP-fusion proteins, (see, e.g., Li et al., U.S. Pat. No. 6,130,313), and fluorescent proteins homologous to GFP, some of which have spectral characteristics different from GFP and emit at yellow and red wavelengths (Matz et al., 1999, Nat. Biotechnol. 17(10): 969-973).

In some embodiments in which it is necessary to employ for a particular cloning step host cells that already display the identifiable characteristic conferred by the portable marker sequence (e.g., when host cells are already resistance to a particular selection agent), an auxiliary marker sequence can be introduced into the insertion cassette to confer a different identifiable characteristic on host cells than the characteristic conferred by the portable marker. This would enable the identification of recombinant host cells containing a recombinant construct resulting from that cloning step.

In some embodiments, an individual marker sequence is provided with target sites that are located within or adjacent to that sequence, and that are recognized by a site-specific recombinase protein that excises the nucleic acid sequence between the target sites, which results in the deletion of at least a portion of the marker sequence or a loss of function if that marker sequence. Illustrative site-specific recombinases include, but are not limited to, Cre, FLP-wild type (wt), FLP-L or FLPe. Recombination may be effected by any art-known method, e.g., the method of Doetschman et al. (1987, Nature 330:576-578); the method of Thomas et al. (1986, Cell 44:419-428); the Cre-loxP recombination system (Sternberg and Hamilton, 1981, J. Mol. Biol. 150:467-486; Lakso et al., 1992, Proc. Natl. Acad. Sci. USA 89:6232-6236); the FLP recombinase system of Saccharomyces cerevisiae (O'Gorman et al., 1991, Science 251:1351-1355; Lyznik et al., 1996, Nucleic Acids Res. 24(19):3784-3789); the Cre-loxP-tetracycline control switch (Gossen and Bujard, 1992, Proc. Natl. Acad. Sci. USA 89:5547-51); and ligand-regulated recombinase system (Kellendonk et al., 1999, J. Mol. Biol. 285:175-82). Desirably, the recombinase is highly active, e.g., the Cre-loxP or the FLPe system, and has enhanced thermostability (Rodrguez et al., 2000, Nature Genetics 25:139-40). In specific embodiments, at least a portion of the marker sequence (including its regulatory sequences, if appropriate) is flanked by either loxP target sites, which are specifically recognised by a Cre recombinase, or FRT target sites, which are specifically recognised by a FLP recombinase. An illustrative example of a loxP target site sequence is 5'-ATAACTTCGTATAGCATACATTATACGAAG TTAT-3' [SEQ ID NO:1]. An illustrative example of an FRT target site sequence is 5'-GAAGTTCCTATTCCGAAGTTCCTAT-TCTCTAGTAAGTATAGGAACTTC -3' [SEQ ID NO:2].

Several other recombination systems are also suitable for use in the present invention. These include, for example, the Gin recombinase of phage Mu (Crisona et al., 1994, J. Mol. Biol. 243(3):437-457), the Pin recombinase of E. coli (see, e.g., Kutsukake et al., 1985, Gene 34(2-3):343-350), the PinB, PinD and PinF from Shigella (Tominaga et al., 1991, J. Bacteriol. 173(13):4079-4087), the R/RS system of the pSR1 plasmid (Araki et al., 1992, J. Mol. Biol. 225(1):25-37) and the cin, hin and β-recombinases. Other recombination systems relevant to this invention described herein are those from Kluyveromyces species, phages, and integrating viruses (e.g., the SSV1-encoded integrase).

In certain embodiments, the recombinase system is linked to a second inducible or repressible transcriptional regulation system. For example, a cell-specific Cre-loxP mediated recombination system (Gossen and Bujard, 1992, Proc. Natl. Acad. Sci. USA 89:5547-51) can be linked to a cell-specific tetracycline-dependent time switch (see, e.g., Ewald et al., 1996, Science 273:1384-1386; Furth et al., 1994, Proc. Natl. Acad. Sci. U.S.A. 91:9302-9306; St-Onge et al., 1996, Nucleic Acids Res. 24(19): 3875-7387). In an illustrative example, an altered cre gene with enhanced expression in mammalian cells is used (Gorski and Jones, 1999, Nucleic Acids Res. 27(9): 2059-2061).

In another illustrative example, the ligand-regulated recombinase system of Kellendonk et al. (1999, J. Mol. Biol. 285: 175-182) is used. In this system, the ligand-binding domain (LBD) of a receptor, is fused to the Cre recombinase to increase specificity of the recombinase. In this way, the activity of the recombinase is controlled by the presence of the ligand in the host cell for the nuclear receptor. The LBD suitably comprises a derivative of part or all of a nuclear receptor, where the part includes the ligand-binding portion of a nuclear receptor. The nuclear receptor may be endogenous to the host cell or may be derived from another species. The nuclear receptor derivative thereof may be selected from the groups comprising steroid-hormone dependent receptors, which include estrogen, androgen, adrenal glucocorticoid, aldosterone and progesterone receptors; nuclear hormone receptors, which include vitamin D, retinoid, thyroid hormone receptors; and orphan nuclear receptors, which include peroxisome proliferator activated receptors and lipid receptors such as, but not limited to, COUP-TFI/II and SF-1. Suitably, the ligand-binding portion of the nuclear receptor is a portion or derivative of a steroid-hormone dependent receptor and is desirably a derivative of the estrogen receptor LBD. Advantageously, the estrogen receptor LBD derivative exhibits reduced or absent affinity for endogenous estrogen and estrogen-related hormones, with reference to a normal, reference range of binding affinity. In certain embodiments of this type, the LBD of the estrogen receptor derivative exhibits affinity for non-endogenous estrogen hormone analogues such as tamoxifen and analogues thereof. The ligand-binding domain may be fused to the N- or C-terminus of the recombinase protein. In specific embodiments, the estrogen-receptor binding domain is fused to the C-terminus of the Cre recombinase protein.

Suitably, individual nucleic acid sequences for the construction of the construct of interest are selected from: (1) a nucleic acid sequence that is homologous with a region of a target site in the genome of a host cell; (2) a transcriptional regulatory element; (3) a translational regulatory element; (4) a sequence that comprises at least one restriction enzyme site; (5) a marker sequence; (6) a sequence that encodes a RNA molecule; (7) a sequence that encodes a polypeptide; (8) a recombination site; (9) an origin of replication; and (10) an antisense molecule.

In some embodiments, therefore, a heterologous nucleic acid sequence is an endogenous polynucleotide that is found naturally in the genome of a host. In other embodiments, the heterologous nucleic acid sequence is a recombinant or artificial nucleic acid. For example, the heterologous nucleic acid sequence may be selected from 1) genes that are both transcribed into mRNA and translated into polypeptides as well as (2) genes that are only transcribed into RNA (e.g., functional RNA molecules such as rRNA, tRNA, RNAi, ribozymes and antisense RNA). In some embodiments, the heterologous nucleic acid sequence encodes a polypeptide for commercial manufacture, where the polypeptide is extracted or purified from the host, host cell or host part. Such polypeptides include, but are not limited to, polypeptides involved in the biosynthesis of antibiotics or secondary metabolites, immunogenic molecules for use in vaccines, cytokines and hormones. In other embodiments, the heterologous nucleic acid sequence encodes a product conferring a beneficial property to the host or other advantageous characteristic including, but not limited to, herbicide resistance or tolerance (e.g., glyphosate resistance or glufosinate resistance), stress tolerance (e.g., salt tolerance), sterility, improved food content or increased yields (e.g., a product affecting starch biosynthesis or modification such as starch branching enzymes, starch synthases, ADP-glucose pyrophosphorylase, products involved in fatty acid biosynthesis such as desaturases or hydroxylases and products altering sucrose metabolism such as invertases, sucrose isomerases or sucrose synthases) as well as disease resistance or tolerance (e.g., resistance to bacterial, viral, nematode, helminth, insect, protozoan or viral pathogens, resistance to cancers or tumors, resistance to autoimmune diseases, illustrative examples of which include: an antigen of tumor, self, bacterial, viral, nematode, helminth, insect, protozoan or viral origin; a product conferring insect resistance such as crystal toxin protein of *Bacillus thuringiensis*; a product conferring viral resistance such as a viral coat or capsid protein; a product conferring fungal resistance such as chitinase, β-1,3-glucanase or phytoalexins).

In other embodiments, the heterologous nucleic acid sequence comprises a promoter, which, in illustrative examples, modulates expression of the marker sequence and optionally the expression of another heterologous nucleic acid sequence. Promoters contemplated by the present invention include constitutive promoters and regulatable promoters, which may be native to a host cell or organism or may be derived from an alternative source, where the promoter is functional in the host cell or organism. The selection of a particular promoter depends on the cell type used to express a nucleic acid sequence to which it is operably connected. Some eukaryotic promoters have a broad host range while others are functional in a limited subset of cell types. Illustrative examples of promoter sequences that function in eukaryotic cells, including mammalian cells, include but are not limited to promoters from the simian virus (e.g., SV40), papilloma virus, adenovirus, human immunodeficiency virus (HIV), rous sarcoma virus, avian sarcoma virus, polyoma, cytomegalovirus, the long terminal repeats (LTR) of moloney leukemia a viral LTR, such as the LTR of the Moloney murine leukemia virus, the early and late promoters of SV40 and the thymidine kinase promoter of herpes simplex virus, the promoters for 3-phosphoglycerate kinase or other glycolytic enzyme genes, the promoters of acid phosphatase genes, e.g., Pho5, as well as the promoters of the hypoxanthine phosphoribosyl transferase (HPTR), adenosine deaminase, pyruvate kinase and β-actin genes. Other illustrative examples of promoters that are functional in prokaryotic or eukaryotic systems include the promoters of the lac system, the trp system, the TAC or TRC system, T7 promoter whose expression is directed by T7 RNA polymerase, the major operator and promoter regions of phage λ, the control regions for fd coat protein, the promoters of the yeast α-mating factors, the polyhedron promoter of the baculovirus system and other sequences known to control the expression of genes of prokaryotic or eukaryotic cells or their viruses, and various combinations thereof.

In certain embodiments, the resulting constructs of interest are useful for expression in plant host cells or for genetically modifying plant genomes and will therefore comprise promoters that are operable in plant cells. Numerous promoters that are active in plant cells have been described in the literature, illustrative examples of which include the nopaline synthase (NOS) promoter, the octopine synthase (OCS) promoter (which is carried on tumour-inducing plasmids of *Agrobacterium tumefaciens*), the caulimovirus promoters such as the cauliflower mosaic virus (CaMV) 19S promoter and the CaMV 35S promoter, the figwort mosaic virus 35S-promoter, the light-inducible promoter from the small subunit of ribulose-1,5-bis-phosphate carboxylase (ssRUBISCO), the Adh promoter, the sucrose synthase promoter, the R gene complex promoter, the GST-II-27 gene promoter and the chlorophyll a/b binding protein gene promoter, etc.

For the purpose of expression in source tissues of the plant, such as the leaf, seed, root or stem, it is sometimes desirable that the promoters driving expression of a particular gene have relatively high expression in these specific tissues. For this purpose, one may choose from a number of promoters for genes with tissue- or cell-specific or enhanced expression. Examples of such promoters include the chloroplast glutamine synthetase GS2 promoter from pea, the chloroplast fructose-1,6-biphosphatase (FBPase) promoter from wheat, the nuclear photosynthetic ST-LS1 promoter from potato, the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine, the promoter for the Cab-1 gene from wheat, the promoter for the CAB-1 gene from spinach, the promoter for the cab1R gene from rice, the pyruvate, orthophosphate dikinase (PPDK) promoter from corn, the promoter for the tobacco Lhcb1*2 gene, the *Arabidopsis thaliana* SUC2 sucrose-H+ symporter and the promoter for the thylakoid membrane proteins from spinach (psaD, psaF, psaE, PC, FNR, atpC, atpD, cab, rbcS). Other promoters for the chlorophyll a/b-binding proteins may also be utilised in the invention, such as the promoters for LhcB gene and PsbP gene from white mustard.

For the purpose of expression in sink tissues of the plant, such as the tuber of the potato plant, the fruit of tomato, or the seed of corn, wheat, rice and barley, it is desirable that the promoters driving expression of the gene of interest have relatively high expression in these specific tissues. A number of promoters for genes with tuber-specific or tuber-enhanced expression are known, including the class I patatin promoter, the promoter for the potato tuber ADPGPP genes, both the large and small subunits, the sucrose synthase promoter, the promoter for the major tuber proteins including the 22 kd protein complexes and protease inhibitors, the promoter for the granule-bound starch synthase gene (GBSS) and other class I and II patatins promoters.

Other promoters can also be used to express a selected gene in specific tissues, such as seeds or fruits. Examples of such promoters include the 5' regulatory regions from such genes as napin, phaseolin, soybean trypsin inhibitor, ACP, stearoyl-ACP desaturase, soybean α' subunit of β-conglycinin (soy 7s), and oleosin. Further examples include the promoter for β-conglycinin. Also included are the zeins, which are a group of storage proteins found in corn endosperm. Genomic clones for zein genes have been isolated and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. Examples of such promoters for barley include those for the ADPGPP subunits, the granule bound and other starch synthase, the branching enzymes, the debranching enzymes, sucrose synthases, the hordeins, the embryo globulins and the aleurone specific proteins.

Root specific promoters may also be used. An example of such a promoter is the promoter for the acid chitinase gene. Expression in root tissue could also be accomplished using the root specific subdomains of the CaMV35S promoter that have been identified.

In certain embodiments, a heterologous nucleic acid sequence comprises a 3' non-translated sequence, which, in illustrative examples, is operably linked to a marker sequence and/or another heterologous nucleotide sequence of interest (which are individually or collectively referred to herein as "construct system polynucleotides") and which functions in the selected host cells to terminate transcription and/or to cause addition of a polyadenylated nucleotide sequence to the 3' end of a RNA sequence transcribed from the construct system polynucleotide(s). Thus, a 3' non-translated sequence refers to that portion of a gene comprising a nucleic acid segment that contains a transcriptional termination signal and/or a polyadenylation signal and any other regulatory signals (e.g., translational termination signals) capable of effecting mRNA processing or gene expression. The polyadenylation signal is characterized by causing the addition of polyadenylic acid tracts to the 3' end of the MRNA precursor. Polyadenylation signals are commonly recognized by the presence of homology to the canonical form 5' AATAAA-3' although variations are not uncommon. The 3' non-translated regulatory sequence desirably includes from about 50 to 1,000 nts and contains transcriptional and translational termination sequences that operable in the host cell.

Transcription of a construct system polynucleotide above the level produced by a selected promoter can be conveniently enhanced using enhancers, which are cis-acting elements of DNA, usually about from 10 to 300 nts that act on a promoter to increase its transcription, and which can define a heterologous nucleic acid sequence of a construct of interest. Enhancers useful for constructing the chimeric constructs of the invention include, but are not limited to, a cytomegalovirus early promoter enhancer, the polyoma enhancer on the late side of the replication origin, and adenovirus enhancers. Examples of transcriptional enhancers for use in plants include, but are not restricted to, elements from the CaMV 35S promoter and octopine synthase genes as for example described by Last et al. (U.S. Pat. No. 5,290,924). It is proposed that the use of an enhancer element such as the ocs element, and particularly multiple copies of the element, will act to increase the level of transcription from adjacent promoters when applied in the context of plant transformation. As transcribed but untranslated leader sequences can influence gene expression, one can also employ a particular leader sequence to enhance expression of a targeting system polynucleotide. Suitable leader sequences include those that comprise sequences selected to direct optimum expression of the targeting system polynucleotide. For example, such leader sequences include a consensus sequence which can increase or maintain mRNA stability and prevent inappropriate initiation of translation as for example described by Joshi (1987, *Nucl. Acid Res.*, 15:6643). However, other leader sequences, e.g., the leader sequence of RTBV, have a high degree of secondary structure that is expected to decrease mRNA stability and/or decrease translation of the mRNA. Thus, leader sequences (i) that do not have a high degree of secondary structure, (ii) that have a high degree of secondary structure where the secondary structure does not inhibit mRNA stability and/or decrease translation, or (iii) that are derived from genes that are highly expressed in plants, will be most desirable. Regulatory elements such as the sucrose synthase intron as, for example, described by Vasil et al. (1989, *Plant Physiol.*, 91:5175), the Adh intron I as, for example, described by Callis et al. (1987, *Genes Develop.*, II), or the TMV omega element as, for example, described by Gallie et al. (1989, *The Plant Cell*, 1:301) can also be included where desired. Other such regulatory elements useful in the practice of the invention are known to those of skill in the art.

These enhancer elements are well known to persons skilled in the art, and can include the ATG initiation codon and adjacent sequences. The initiation codon must be in phase with the reading frame of the coding sequence relating to the foreign or endogenous DNA sequence to ensure translation of the entire sequence. The translation control signals and initiation codons can be of a variety of origins, both natural and synthetic. Translational initiation regions may be provided from the source of the transcriptional initiation region, or from the foreign or endogenous DNA sequence. The sequence can also be derived from the source of the promoter selected to drive transcription, and can be specifically modified so as to increase translation of the mRNA.

Additionally, a heterologous nucleic acid sequence can be selected from targeting sequences that target a protein product of a construct system polynucleotide (e.g., marker sequence product or expression product of another heterologous nucleotide sequence of interest) to an intracellular compartment within cells or to the extracellular environment. For example, a nucleic acid sequence encoding a transit or signal peptide sequence may be operably linked to a sequence encoding a desired protein such that, when translated, the transit or signal peptide can transport the protein to a particular intracellular or extracellular destination, respectively, and can then be post-translationally removed. Transit or signal peptides act by facilitating the transport of proteins through intracellular membranes, e.g., periplasm, vacuole, vesicle, plastid and mitochondrial membranes, whereas signal peptides direct proteins through the extracellular membrane. For example, the transit or signal peptide can direct a desired protein to a particular organelle such as a plastid (e.g., a chloroplast), rather than to the cytoplasm. Thus, a construct of the invention can further comprise a plastid transit peptide encoding nucleic acid sequence operably linked between a promoter and the construct system polynucleotide. For example, reference may be made to Heijne et al. (1989, *Eur. J. Biochem.*, 180:535) and Keegstra et al. (1989, *Ann. Rev. Plant Physiol. Plant Mol. Biol.*, 40:471).

A construct of the invention can define or can be introduced into a vector, such as a plasmid. Plasmid vectors include additional nucleic acid sequences that provide for easy selection, amplification, and transformation of the expression cassette in prokaryotic and eukaryotic cells, non-limiting examples of which include pUC-derived vectors, pSK-derived vectors, pGEM-derived vectors, pSP-derived vectors, or pBS-derived vectors. Additional nucleic acid sequences include origins of replication to provide for autonomous replication of the vector, selectable marker genes, desirably encoding antibiotic or herbicide resistance, unique multiple cloning sites providing for multiple sites to insert nucleic acid sequences or genes encoded in the chimeric construct and sequences that enhance transformation of prokaryotic and eukaryotic cells.

For autonomous replication, the vector may further comprise an origin of replication enabling the vector to replicate autonomously in the host cell in question. Non-limiting examples of bacterial origins of replication include the origins of replication of plasmids pBR322, pUC19, pACYC177, and pACYC184 permitting replication in *E. coli*, and pUB110, pE194, pTA1060, and PAMβ1 permitting replication in *Bacillus*. The origin of replication may be one having a mutation to make its function temperature-sensitive in a *Bacillus* cell (see, e.g., Ehrlich, 1978, *Proc. Natl. Acad. Sci. USA* 75:1433).

In specific embodiments, the construct of interest is a targeting construct. For example, the targeting construct can be organized such that a marker sequence, usually a selectable marker gene, is operatively positioned between two flanking portions of a targeting cassette, which are sufficiently homologous with regions of a target site in the cellular genome to permit homologous recombination between the targeting cassette and the target site. For example, the target site may comprise an endogenous gene (e.g., comprising an exonic or coding sequence or a sequence encoding a functional RNA) and in certain embodiments, the marker sequence is positioned by the flanking portions of the targeting cassette to disrupt or replace at least a portion of the endogenous gene thereby rendering the endogenous gene inactive and thus non-functional. In these embodiments, one of the flanking portions may be substantially homologous to at least a portion of the 5' untranslated sequence of the endogenous gene, and the other substantially homologous to at least a portion of the 3' untranslated sequence of the endogenous gene. Generally, such a non-conditional knock-out approach is used when targeting a small gene. Site-specific homologous recombination between the targeting construct and the target site subsequently results in replacement of at least a portion of the endogenous gene with the marker gene. In these instances, the targeting construct is used to produce knockout organisms having a partial or complete loss of function in at least one allele of the endogenous gene.

In other embodiments, the targeting cassette further comprises a foreign or exogenous nucleotide sequence of interest (e.g., a foreign gene or regulatory element, or portion thereof) between the flanking portions of the cassette. For example, the nucleotide sequence of interest is positioned by the flanking portions of the targeting cassette to replace at least a portion of the endogenous gene with the nucleotide sequence of interest to produce an altered or modified endogenous gene or to replace the endogenous gene with the nucleotide sequence of interest or to introduce novel regulatory elements in operable connection with the endogenous gene. In other examples, the nucleotide sequence of interest is positioned by the flanking portions of the targeting cassette to replace a region of the genome (e.g., an intergenic sequence) that does not include gene sequences such as exons or coding sequences, introns, untranslated regions of exons or regulatory element regions such as promoters. In this scenario, cells can be selected that have undergone site-specific homologous recombination at a locus without inactivating that particular locus. In other examples, the nucleotide sequence of interest is positioned by the flanking portions of the targeting cassette for introduction within an intron or non-coding region of the genome such that the introduction does not disrupt regulatory, exonic or coding sequences. In these examples, one of the flanking portions may be substantially homologous to an exon and portion of an intron of an endogenous gene, and the other substantially homologous to a portion of an intron and a downstream exon. Site-specific homologous recombination between the targeting construct and cellular endogenous genomic target sequences subsequently results in the positioning of the nucleotide sequence of interest within the intron and thus not disrupting critical exonic coding sequences. A requirement of this scenario is that the nucleotide sequence of interest must be under the control of regulatory elements present within the targeting cassette. In still other examples, the nucleotide sequence of interest lacks an upstream promoter in the targeting cassette and is positioned by the flanking portions of the targeting cassette for insertion into a region of the genome that is downstream of endogenous cellular regulatory elements. In these examples, one of the flanking portions may be substantially homologous to a promoter and portion of a 5' untranslated region and the other substantially homologous to an intron and downstream exon. In this scenario, the targeting construct is designed to drive transcription of the nucleotide sequence of interest under the control of regulatory elements endogenous to the particular gene targeted by the targeting construct. Homologous recombination between the targeting construct and the target site provides regulatory elements specific for the targeted gene which subsequently drive the transcription of the nucleotide sequence of interest. The nucleotide sequence of interest will most often not be transcribed unless site-specific homologous recombination occurs, thereby providing endogenous cellular regulatory elements sufficient to drive transcription of these sequences. Additionally, it will be readily apparent to those of skill in the art that a targeting construct can be engineered to express more than one nucleotide sequence of interest or transgene, which can be the same (for example to increase the effective gene dosage) or different to achieve complementary effects. Each transgene can be under control of the same promoter (for example, through the use of internal ribosomal entry site (IRES) elements) or different promoters. IRES elements function as initiators of the efficient translation of reading frames. In particular, an IRES allows for the translation of two different genes on a single transcript and greatly facilitates the selection of cells expressing the transgenes at uniformly high levels. IRES elements are known in the art, illustrative examples of which include those IRES elements from poliovirus Type I, the 5'UTR of encephalomyocarditis virus (EMV), of "Thelier's murine encephalomyelitis virus" (TMEV), of "foot and mouth disease virus" (FMDV) of "bovine enterovirus" (BEV), of "coxsackie B virus" (CBV), or of "human rhinovirus" (HRV), or the "human immunoglobulin heavy chain binding protein" (BIP) 5'UTR, the *Drosophila antennapediae* 5'UTR or the *Drosophila ultrabithorax* 5'UTR, or genetic hybrids or fragments from the above-listed sequences. See also, e.g., Kim et al., 1992, *Molecular and Cellular Biology* 12(8): 3636-3643; McBratney et al., 1993, *Current Opinion in Cell Biology* 5: 961-965; Oh and Sarnow, 1993, *Current Opinion in Genetics and Development* 3: 295-300; and Ramesh et al., 1996, *Nucleic Acids Research* 24:2697-2700. In the above instances, the targeting constructs are suitable for producing transgenic or knock-in organisms containing at least one copy of the nucleotide sequence of interest in the genome of the organism.

Various host cells are contemplated for producing the subject chimeric constructs and will include prokaryotic and eukaryotic hosts. In certain embodiments, the host cell type is capable of undergoing site-specific homologous recombination. Representative prokaryotic hosts include, but are not limited to, bacteria. Illustrative examples of eukaryotic hosts include, but are not limited to, fungi such as yeast and filamentous fungi, including species of *Aspergillus, Trichoderma*, and *Neurospora*; animal hosts including vertebrate animals illustrative examples of which include fish (e.g., salmon, trout, tulapia, tuna, carp, flounder, halibut, swordfish, cod and zebrafish), birds (e.g., chickens, ducks, quail, pheasants and turkeys, and other jungle foul or game birds) and mammals (e.g., dogs, cats, horses, cows, buffalo, deer, sheep, rabbits, rodents such as mice, rats, hamsters and guinea pigs, goats, pigs, primates, marine mammals including dolphins and whales, as well as cell lines, such as human or other mammalian cell lines of any tissue or stem cell type (e.g., COS, NIH 3T3 CHO, BHK, 293, or HeLa cells), and stem cells, including pluripotent and non-pluripotent and embryonic stem cells, and non-human zygotes), as well as invertebrate animals illustrative examples of which include nematodes (representative generae of which include those that infect animals such as but not limited to *Ancylostoma, Ascaridia, Ascaris, Bunostomum, Caenorhabditis, Capillaria, Chabertia, Cooperia, Dictyocaulus, Haernonchus, Heterakis, Nematodirus, Oesophagostomum, Ostertagia, Oxyuris, Parascaris, Strongylus, Toxascaris, Trichuris, Trichostrongylus, Tflichonema, Toxocara, Uncinaria*, and those that infect plants such as but not limited to *Bursaphalenchus, Criconeriella, Diiylenchus, Ditylenchus, Globodera, Helicotylenchus, Heterodera, Longidorus, Melodoigyne, Nacobbus, Paratylenchus, Pratylenchus, Radopholus, Rotelynchus, Tylenchus*, and *Xiphinerna*) and other worms, drosophila, and other insects (such as from the families Apidae, Curculionidae, Scarabaeidae, Tephritidae, Tortricidae, amongst others, representative orders of which include Coleoptera, Diptera, Lepidoptera, and Homoptera).

In certain embodiments, the host is a plant which is suitably selected from monocotyledons, dicotyledons and gymnosperms. The plant may be an ornamental plant or crop plant. Illustrative examples of ornamental plants include, but are not limited to, *Malus* spp, *Crataegus* spp., *Rosa* spp., *Betula* spp, *Sorbus* spp, *Olea* spp, *Nerium* spp, *Salix* spp, *Populus* spp. Illustrative examples of crop plants include plant species which are cultivated in order to produce a harvestable product such as, but not limited to, *Abelmoschus esculentus* (okra), *Acacia* spp., *Agavefourcroydes* (henequen), *Agave sisalana* (sisal), *Albizia* spp., *Allium fistulosum* (bunching onion), *Allium sativum* (garlic), *Allium* spp. (onions), *Alpinia galanga* (greater galanga), *Amaranthus caudatus, Amarantlius* spp., *Anacardium* spp. (cashew), *Ananas comosus* (pineapple), *Anethum graveolens* (dill), *Annona cherimola* (cherimoya), *Apios americana* (American potatobean), *Arachis hypogaea* (peanut), *Arctium* spp. (burdock), *Artemisia* spp. (wormwood), *Aspalathus linearis* (redbush tea), *Athertonia diversifolia, Atriplex nummularia* (old man saltbush), *Averrhoa carambola* (starfruit), *Azadirachta indica* (neem), *Backhousia* spp., *Bambusa* spp. (bamboo), *Beta vulgaris* (sugar beet), *Boehmeria nivea* (ramie), *bok choy, Boronia megastigma* (sweet boronia), *Brassica carinata* (Abyssinian mustard), *Brassica juncea* (Indian mustard), *Brassica napus* (rapeseed), *Brassica oleracea* (cabbage, broccoli), *Brassica oleracea* var *Albogabra* (gai lum), *Brassica parachinensis* (choi sum), *Brassica pekensis* (Wong bok or Chinese cabbage), *Brassica* spp., *Burcella obovata, Cajanus cajan* (pigeon pea), *Camellia sinensis* (tea), *Cannabis sativa* (non-drug hemp), *Capsicum* spp., *Carica* spp. (papaya), *Carthamus tinctorius* (safflower), *Carum carvi* (caraway), *Cassinia* spp., *Castanospermum australe* (blackbean), *Casuarina cunninghamiana* (beefwood), *Ceratonia siliqua* (carob), *Chamaemelum nobile* (chamomile), *Chamelaucium* spp. (Geraldton wax), *Chenopodium quinoa* (quinoa), *Chrysanthemum* (Tanacetum), *cinerarifolium* (pyrethrum), *Cicer arietinum* (chickpea), *Cichorium intybus* (chicory), *Clematis* spp., *Clianthus formosus* (Sturt's desert pea), *Cocos nucifera* (coconut), *Coffea* spp. (coffee), *Colocasia esculenta* (taro), *Coriandrum sativum* (coriander), *Crambe abyssinica* (crambe), *Crocus sativus* (saffron), *Cucurbita foetidissima* (buffalo gourd), *Cucurbita* spp. (gourd), *Cyamopsis tetragonoloba* (guar), *Cymbopogon* spp. (lemongrass), *Cytisus proliferus* (tagasaste), *Daucus carota* (carrot), *Desmanthus* spp., *Dioscorea esculenta* (Asiatic yam), *Dioscorea* spp. (yams), *Diospyros* spp. (persimmon), *Doronicum* sp., *Echinacea* spp., *Eleocharis dulcis* (water chestnut), *Eleusine coracana* (finger millet), *Emanthus arundinaceus, Eragrostis tef* (tef), *Erianthus arundinaceus, Eriobotrya japonica* (loquat), *Eucalyptus* spp., *Eucalyptus* spp. (gil mallee), *Euclea* spp., *Eugenia malaccensis* (jumba), *Euphorbia* spp., *Euphoria longana* (longan), *Eutrema wasabi* (wasabi), *Fagopyrum esculentum* (buckwheat), *Festuca arundinacea* (tall fescue), *Ficus* spp. (fig), *Flacourtia inermis, Flindersia grayliana* (Queensland maple), *Foeniculum olearia, Foeniculum vulgare* (fennel), *Garcinia mangostana* (mangosteen), *Glycine latifolia, Glycine max* (soybean), *Glycine max* (vegetable soybean), *Glycyrrhiza glabra* (licorice), *Gossypium* spp. (cottons), *Grevillea* spp., *Grindelia* spp., *Guizotia abyssinica* (niger), *Harpagophyllum* sp., *Helianthus annuus* (high oleic sunflowers), *Helianthus annuus* (monosun sunflowers), *Helianthus tuberosus* (Jerusalem artichoke), *Hibiscus cannabinus* (kenaf), *Hordeum bulbosum, Hordeum* spp. (waxy barley), *Hordeum vulgare* (barley), *Hordeum vulgare* subsp. *spontaneum, Humulus lupulus* (hops), *Hydrastis canadensis* (golden seal), *Hymenachne* spp., *Hyssopus officinalis* (hyssop), *Indigofera* spp., *Inga edulis* (ice cream bean), *Inocarpus tugiter, Ipomoea batatas* (sweet potato), *Ipomoea* sp. (kang kong), *Lablab purpureus* (white lablab), *Lactuca* spp. (lettuce), *Lathyrus* spp. (vetch), *Lavandula* spp. (lavender), *Lens* spp. (lentil), *Lesquerella* spp. (bladderpod), *Leucaena* spp.,

*Lilium* spp., *Limnanties* spp. (meadowfoam), *Linum usitatissimum* (flax), *Linum usitatissimum* (linseed), *Linum usitatissimum* (Linola.TM.), *Litchi chinensis* (lychee), *Lotus corniculatus* (birdsfoot trefoil), *Lotus pedunculatus, Lotus* sp., *Luffa* spp., *Lunaria annua* (honesty), *Lupinus mutabilis* (pearl lupin), *Lupinus* spp. (lupin), *Macadamia* spp., *Mangifera indica* (mango), *Manihot esculenta* (cassava), *Medicago* spp. (lucerne), *Medicago* spp., *Melaleuca* spp. (tea tree), *Melaleuca uncinata* (broombush), *Mentha tasmannia, Mentha spicata* (spearmint), *Mentha Xpiperita* (peppermint), *Momordica charantia* (bitter melon), *Musa* spp. (banana), *Myrciaria cauliflora* (jaboticaba), *Myrothamnus flabellifolia, Nephelium lappaceum* (rambutan), *Nerine* spp., *Ocimum basilicum* (basil), *Oenanthe javanica* (water dropwort), *Oenothera biennis* (evening primrose), *Olea europaea* (olive), *Olearia* sp., *Origanum* spp. (marjoram, oregano), *Oryza* spp. (rice), *Oxalis tuberosa* (oca), *Ozothamnus* spp. (rice flower), *Pachyrrhizus ahipa* (yam bean), *Panax* spp. (ginseng), *Panicum miliaceum* (common millet), *Papaver* spp. (poppy), *Parthenium argentatum* (guayule), *Passiflora* sp., *Paulownia tomemtosa* (princess tree), *Pelargonium graveolens* (rose geranium), *Pelargonium* sp., *Pennisetum americanum* (bulrush or pearl millet), *Persoonia* spp., *Petroselinum crispum* (parsley), *Phacelia tanacetifolia* (tansy), *Phalaris canariensis* (canary grass), *Phalaris* sp., *Phaseolus coccineus* (scarlet runner bean), *Phaseolis lunatus* (lima bean), *Phaseolus* spp., *Phaseolus vulgaris* (culinary bean), *Phaseolus vulgaris* (navy bean), *Phaseolus vulgaris* (red kidney bean), *Pisum sativum* (field pea), *Plantago ovata* (psyllium), *Polygonum minus, Polygonum odoratum, Prunus mume* (Japanese apricot), *Psidium guajava* (guava), *Psophocarpus tetragonolobus* (winged bean), *Pyrus* spp. (nashi), *Raphanus satulus* (long white radish or Daikon), *Rhagodia* spp. (saltbush), *Ribes nigrum* (black currant), *Ricinus communis* (castor bean), *Rosmarinus officinalis* (rosemary), *Rungia klossii* (rungia), *Saccharum officinarum* (sugar cane), *Salvia officinalis* (sage), *Salvia sclarea* (clary sage), *Salvia* sp., *Sandersonia* sp., *Santalum acuminatum* (sweet quandong), *Santalum* spp. (sandalwood), *Sclerocarya caffra* (marula), *Scutellaria galericulata* (scullcap), *Secale cereale* (rye), *Sesamum indicum* (sesame), *Setaria italica* (foxtail millet), *Simmondsia* spp. (jojoba), *Solanum* spp., *Sorghum almum* (sorghum), *Stachys betonica* (wood betony), *Stenanthemum scortechenii, Strychnos cocculoides* (monkey orange), *Stylosanthes* spp. (stylo), *Syzygium* spp., *Tasmannia lanceolata* (mountain pepper), *Terminalia karnbachii, Theobroma cacao* (cocoa), *Thymus vulgaris* (thyme), *Toona australis* (red cedar), *Trifolium* spp. (clovers), *Trifolium alexandrinum* (berseem clover), *Trifolium resupinatum* (persian clover), *Triticum* spp., *Triticum tauschii, Tylosema esculentum* (morama bean), *Valeriana* sp. (valerian), *Vernonia* spp., *Vetiver zizanioides* (vetiver grass), *Vicia benghalensis* (purple vetch), *Viciafaba* (faba bean), *Vicia narbonensis* (narbon bean), *Vicia sativa, Vicia* spp., *Vigna aconitifolia* (mothbean), *Vigna angularis* (adzuki bean), *Vigna mungo* (black gram), *Vigna radiata* (mung bean), *Vigna* spp., *Vigna unguiculata* (cowpea), *Vitis* spp. (grapes), *Voandzeia subterranea* (bambarra groundnut), *Triticosecale* (triticale), *Zea mays* (bicolour sweetcorn), *Zea mays* (maize), *Zea mays* (sweet corn), *Zea mays* subsp. *mexicana* (teosinte), *Zieria* spp., *Zingiber officinale* (ginger), *Zizania* spp. (wild rice), *Ziziphus jujuba* (common jujube). Desirable crops for the practice of the present invention include *Nicotiana tabacum* (tobacco) and horticultural crops such as, for example, *Ananas comosus* (pineapple), *Saccharum* spp (sugar cane), *Musa* spp (banana), *Lycopersicon esculentum* (tomato) and *Solanum tuberosum* (potato).

Advantageously, the portable marker sequence employed for chaperoning the heterologous nucleic acid sequences from one recipient construct to another, confers an identifiable characteristic in at least two different host cell types. For example, in certain embodiments, various cloning steps can be performed in bacterial host cells and others in mammalian host cells. In these instances, it is desirable to use a single marker sequence for conferring the identifiable characteristic in both the bacterial and mammalian host cell types. Illustrative examples of such marker sequences include selectable marker genes such as but not limited to kanamycin/neomycin resistance genes and screenable marker genes, illustrative examples of which include GFP and luciferase.

The constructs of the invention are introduced into a host by any suitable means including "transduction" and "transfection", which are art recognized as meaning the introduction of a nucleic acid, e.g., an expression vector, into a recipient cell by nucleic acid-mediated gene transfer. "Transformation", however, refers to a process in which a host's genotype is changed as a result of the cellular uptake of exogenous DNA or RNA, and, for example, the transformed cell comprises the expression system of the invention. There are many methods for introducing targeting constructs into cells. Typically, the method employed will depend on the choice of host cell. Technology for introduction of targeting constructs into host cells is well known to those of skill in the art. Four general classes of methods for delivering nucleic acid molecules into cells have been described: (1) chemical methods such as calcium phosphate precipitation, polyethylene glycol (PEG)-mediate precipitation and lipofection; (2) physical methods such as microinjection, electroporation, acceleration methods and vacuum infiltration; (3) vector based methods such as bacterial and viral vector-mediated transformation; and (4) receptor-mediated. Transformation techniques that fall within these and other classes are well known to workers in the art, and new techniques are continually becoming known. The particular choice of a transformation technology will be determined by its efficiency to transform certain host species as well as the experience and preference of the person practising the invention with a particular methodology of choice. It will be apparent to the skilled person that the particular choice of a transformation system to introduce a targeting construct into cells is not essential to or a limitation of the invention, provided it achieves an acceptable level of nucleic acid transfer.

Thus, the constructs of the invention are introduced into tissues or host cells by any number of routes, including viral infection, microinjection, electroporation, or fusion of vesicles. Jet injection may also be used for intra-muscular administration (as described for example by Furth et al., *Anal Biochem* 205:365-368 (1992)). The constructs may be coated onto microprojectiles, and delivered into a host cell or into tissue by a particle bombardment device, or "gene gun" (see, for example, Tang et al., *Nature* 356:152-154 (1992)). Alternatively, the constructs can be fed directly to, or injected into, the host organism or it may be introduced into the cell (i.e., intracellularly) or introduced extracellularly into a cavity, interstitial space, into the circulation of an organism, introduced orally, etc. Methods for oral introduction include direct mixing of the targeting constructs with food of the organism. In certain embodiments, a hydrodynamic nucleic acid administration protocol is employed (e.g., see Chang et al., 2001, *J. Virol.* 75:3469-3473; Liu et al., 1999, *Gene Ther.* 6:1258-1266; Wolff et al., 1990, *Science* 247:1465-1468; Zhang et al., 1999, *Hum. Gene Ther.* 10:1735-1737; and Zhang et al., 1999, Gene Ther. 7:1344-1349).

Certain embodiments of the present invention are concerned with introducing the constructs of the invention into plant cells. Guidance in the practical implementation of transformation systems for plant improvement is provided, for example, by Birch (1997, *Annu. Rev. Plant Physiol. Plant Molec. Biol.* 48: 297-326). Thus, in these embodiments, recipient plant cells are employed that are susceptible to transformation and subsequent regeneration into stably transformed, fertile plants. For monocot transformation for example, immature embryos, meristematic tissue, gametic tissue, embryogenic suspension cultures or embryogenic callus tissue can be employed as a source of recipient cells which is useful in the practice of the invention. For dicot transformation, organ and tissue cultures can be employed as a source of recipient cells. Thus, tissues, e.g., leaves, seed and roots, of dicots can provide a source of recipient cells useful in the practice of the invention. Cultured susceptible recipient cells are suitably grown on solid supports. Nutrients are provided to the cultures in the form of media and the environmental conditions for the cultures are controlled. Media and environmental conditions which support the growth of regenerable plant cultures are well known to the art.

In principle both dicotyledonous and monocotyledonous plants that are amenable to transformation, can be modified by introducing a construct of the invention into a recipient cell and growing a new plant that harbors the construct of the invention. Illustrative transformation methods include Agrobacterium-mediated transfer, Cauliflower mosaic virus (CaMV)-mediated transfer, electroporation, microprojectile bombardment, microinjection, calcium phosphate precipitation or polyethylene glycol precipitation, pollen-mediated transfer or combination thereof Transformation techniques that fall within these and other classes are well known to workers in the art, and the particular choice of a transformation technology will be determined by its efficiency to transform the selected host species.

The present invention also contemplates host cells in which the constructs of the invention have been introduced. In addition, the presently described invention includes genetically modified organisms, including genetically modified plants and non-human animals which have been derived from cells in which the constructs of the invention have been introduced.

The invention also contemplates kits for sequential cloning of a plurality of nucleic acid sequences. In some embodiments, the kits comprise a donor marker construct that comprises a portable cassette that lacks an origin of replication but comprises a marker sequence that confers an identifiable characteristic on host cells that contain the marker sequence. The donor marker construct may include an origin of replication elsewhere in the vector to permit autonomous replication of the donor vector in compatible host cells. In certain advantageous embodiments, the origin of replication is inactivatable, for example by being destroyed or otherwise weakened, so that its function is abrogated or impaired and is thus unable to substantially permit autologous recombination in a host cell. Suitably, this impaired or loss of function is achieved by restriction endonuclease cleavage or site specific mutagenesis of the origin of replication or sequences adjacent to that origin that affect its functional activity. The portable cassette is desirably flanked by one or more restriction enzyme sites for convenient excision and subsequent insertion into a recipient construct of interest. In illustrative examples, the kit comprises a plurality of donor marker vectors each comprising at least one different restriction enzyme site for excising a respective portable cassette than a corresponding restriction enzyme site of another donor marker vector. In these examples, individual donor marker vectors are used to provide a portable cassette with different types of ends to match those of a particular recipient construct into which the portable cassette will be inserted. In some embodiments, individual donor marker vectors include a topoisomerase recognition sequence on at least one end of the portable segment as a substrate for topoisomerase-dependent insertion of the portable segment into a recipient construct of interest.

In some embodiments, the kits further comprise a first recipient construct that lacks the marker sequence but comprises at least one cloning site into which a nucleic acid sequence is insertable and into which the portable cassette is insertable, wherein the nucleic acid sequence and the portable cassette when inserted into their corresponding cloning site(s) on the first recipient construct yield another cassette that is optionally portable into another recipient construct. In some examples, an individual cloning site comprises at least one restriction enzyme site, whilst in others it comprises or defines a substrate for topoisomerase-mediated joining. Typically, the first recipient construct will comprise an origin of replication as well as another marker sequence that confers a different identifiable characteristic than that conferred by the marker sequence of the portable cassette. In illustrative examples of this type, the other marker sequence comprises a selectable marker gene (e.g., an ampicillin resistance gene) or a screenable marker gene (e.g., a fluorescent marker gene such as EGFP or a enzymatic marker gene such as lacZ).

In some embodiments, the kits further comprise a third recipient construct that lacks the marker sequence but comprises at least one cloning site into which another nucleic acid sequence is insertable and into which the other cassette is insertable, wherein the other nucleic acid sequence and the other cassette when inserted into their corresponding cloning site(s) on the second recipient construct yield a further cassette that is optionally portable into another recipient construct. Suitably, the kits further comprise at least one additional recipient construct that lacks the marker sequence but comprises at least one cloning site into which a further nucleic acid sequence is insertable and into which the further cassette is insertable, wherein the further nucleic acid sequence and the further cassette when inserted into their corresponding cloning site(s) on the additional recipient construct(s) yield another cassette that is optionally portable into a recipient construct. In illustrative examples of this type, the kits comprise at least 1, 2, 3, 4, 5, 6, 7, 8, 9, 1 0 times, even at least 15, 20, 25, 30 or more additional recipient construct(s).

In some embodiments in which constructs comprises recombinase recognition sequences, the kits further comprise a construct that comprises a nucleic acid sequence from which a recombinase protein is expressible.

In some embodiments, the marker sequence is flanked by recombinase target sites, which are recognized by a recombinase protein that mediates excision of the marker sequence from a construct in which it resides. Suitably, the target sites are selected from loxP sites and FRT sites.

In some embodiments, the kits comprise at least one donor marker construct comprising a portable segment that lacks an origin of replication but comprises a marker sequence that confers an identifiable characteristic on host cells that contain the marker sequence, wherein the portable cassette is excisable using a plurality of different excising agents or more such that the portable cassette when excised using at least one of the excising agents has different ends than when excised using at least one other of the excising agents. Suitably, the portable cassette is flanked on each side by a plurality of different recognition sites (e.g., at least 2, 3, 4, 5, 6, 7, 8, 9, 10 or more). In illustrative examples of this type, each recognition site is cleavable by a different endonuclease and thus include, for example, a plurality of different endonuclease cleavage sites (e.g., those defining multiple cloning sites). Alternatively, or in addition, the portable cassette is flanked on each side by a plurality of recombinase target sites, each recognized by a different recombinase protein. In these embodiments, an individual donor marker construct provides a choice of excising agents to provide the portable cassette with ends that are compatible with the cloning site of a recipient construct of interest.

Generally, the kits will further include instructions for carrying out the steps of the method of the invention, an illustrative example of which is set forth in Example 14. Such kits may also include restriction endonucleases as well as the appropriate reaction buffers for their use and the use of other enzymes, such as DNA ligases, Shrimp Alkaline Phosphatases (SAP), topoisomerases and DNA polymerases, in the method of the invention. In illustrative examples, the kits may further include a protocol for using the contents of a kit to perform homologous recombination. Furthermore, the kits may comprise competent bacterial host cells, e.g. *E. coli* cells or particular eukaryotic cells or cell lines.

In order that the invention may be readily understood and put into practical effect, particular preferred embodiments will now be described by way of the following non-limiting examples.

EXAMPLES

Example 1

Pelle Cloning System

The "Pelle" cloning system represents one embodiment of the cloning system broadly described above. The Pelle cassette shown in FIG. 1, comprises a neomycin phosphotransferase gene (Neo), which is located downstream of the bacterial EM7 promoter (EM7) and the mammalian PGK promoter (PGK), and upstream of a bovine growth hormone (BGH) polyadenylation signal (pA) for proper termination and processing of the Neo transcript (FIG. 1).

The Neo gene of the Pelle cassette is under the control of the bacterial EM7 promoter, providing kanamycin resistance in bacteria. In this example, the Pelle cassette forms part of a Pelle donor plasmid that comprises an ampicillin resistance gene. Consequently, the Pelle donor plasmid is resistant to both kanamycin and ampicillin under selection. The recipient construct or vector into which the Pelle cassette is insertable does not confer kanamycin resistance. Before insertion of the Pelle cassette into the recipient vector, the ampicillin gene in the donor vector is disrupted by digesting the donor vector with restriction endonuclease AcII; in addition to treating the digested donor vector with shrimp alkaline phosphatase to further prevent self religation through dephosphorylation.

Figure 2:
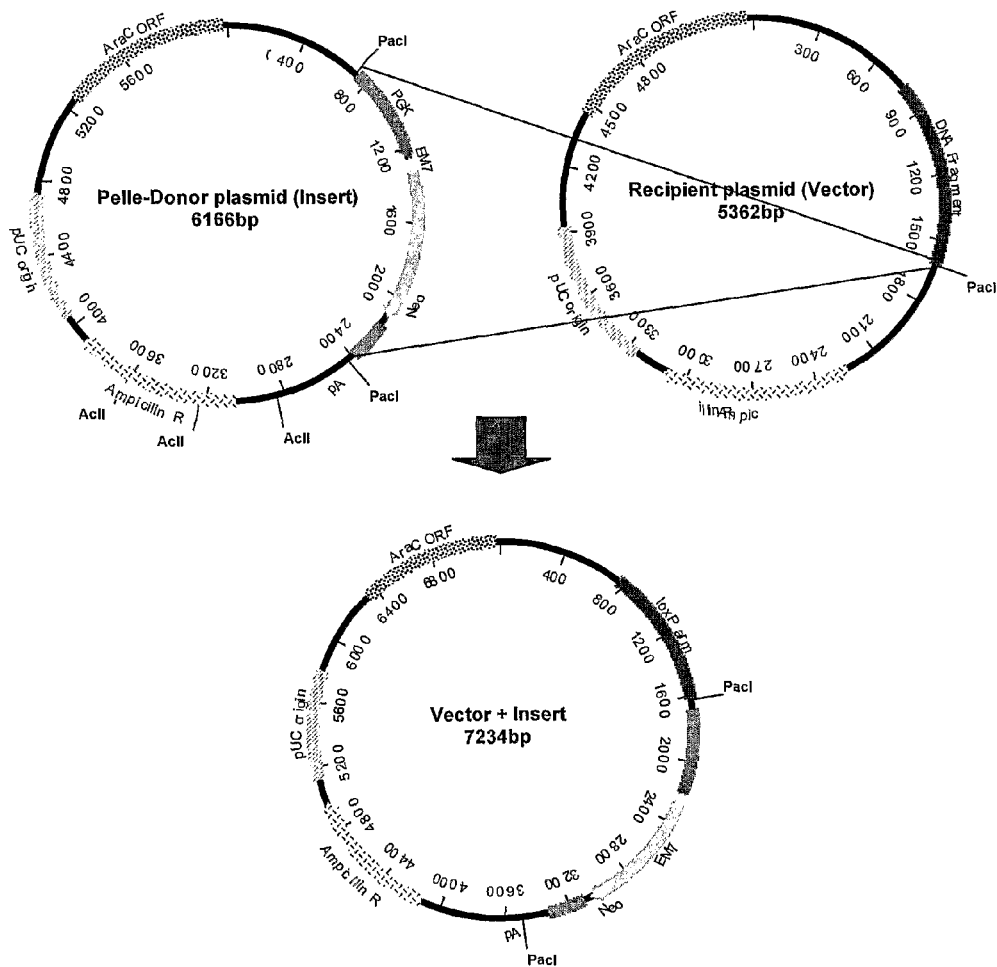
FIG. 2 is a diagrammatic representation showing the cloning of the Pelle insert cassette from a Pelle donor plasmid into a recipient vector to produce a recombinant vector containing the Pelle cassette.

The Pelle cassette is ligated into the arms of a linearized recipient plasmid that comprises an ampicillin resistance gene as well as a DNA fragment that will form part of a nucleic acid construct of interest (see FIG. 2). Recombinant plasmids are introduced into *E. coli* host cells, which are cultured in the presence of kanamycin to select for those that are resistant. This selection effectively eliminates colonies containing only the recipient vector or the backbone of the Pelle donor vector, leaving only colonies containing the Pelle cassette inserted into the recipient vector. Minimal background colonies are observed from a donor only control ligation (generally comprising <10% and typically <1% of colony numbers resulting from a recipient and donor ligation). These colonies result from self religation of the Pelle cassette with the donor vector backbone due to inefficiencies of restriction endonucleases.

Figure 3:
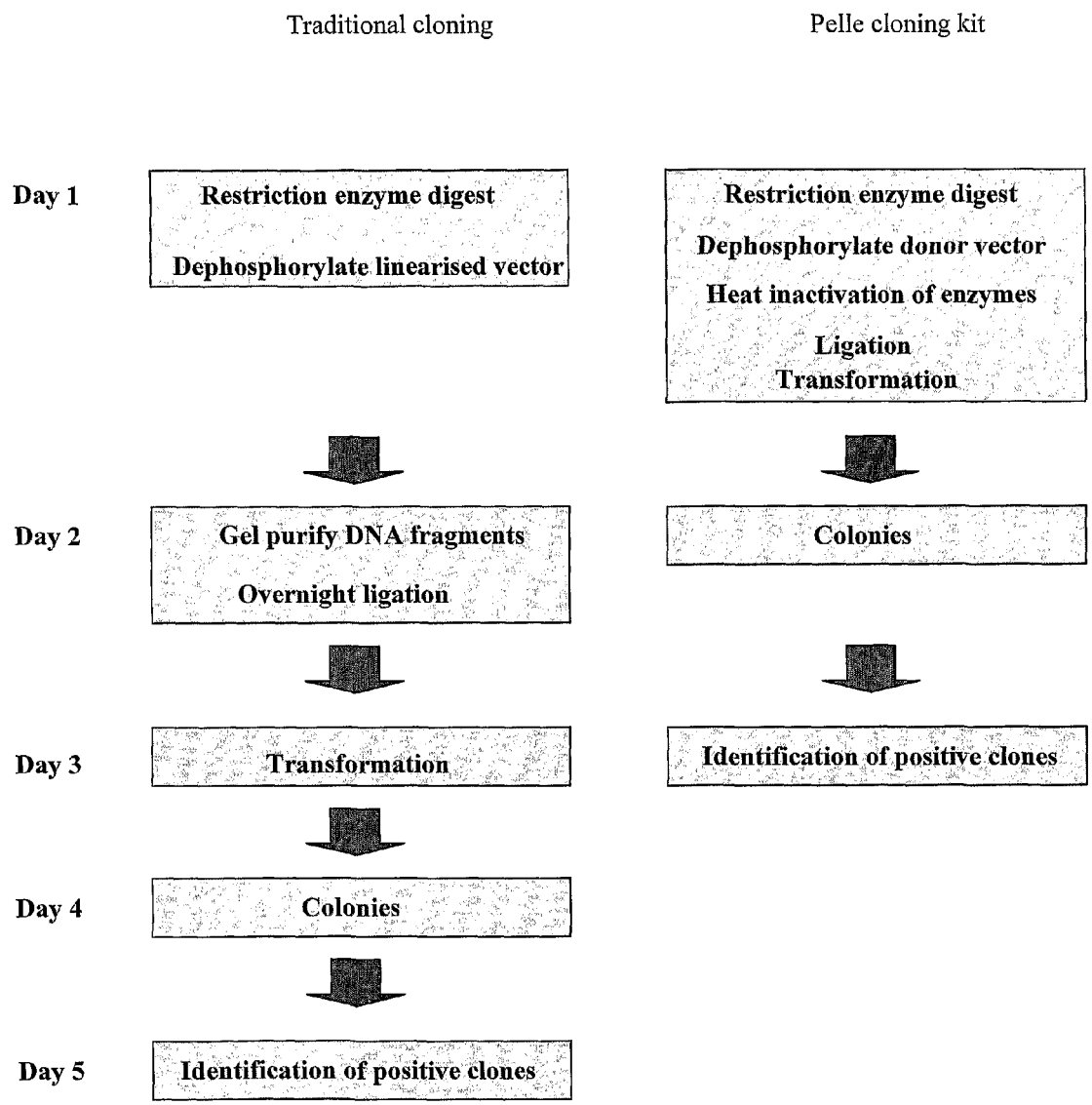
FIG. 3 is a diagrammatic representation showing a temporal comparison of the Pelle cloning system and a traditional cloning system.
Figure 4:
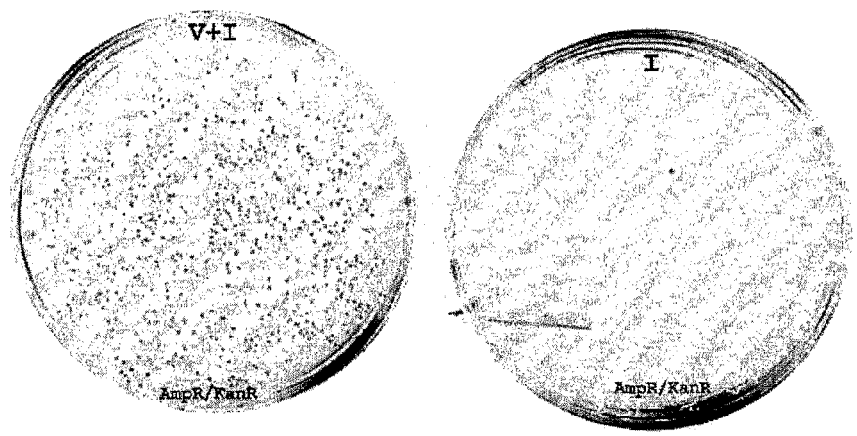
FIG. 4 is photographical representation showing the enrichment of recombinant colonies achieved using the Pelle cloning system. Panel A shows a first agar plate with a large number of recombinant colonies after selection on ampicillin and kanamycin, whilst virtually no background colonies were obtained on a second agar plate under the same selection criteria, containing donor vector alone. Panel B shows a restriction enzyme digest analysis of six colonies from the first plate in which two recombinant vectors were obtained with the Pelle cassette in one orientation (Clones 2 and 5) and four recombinant vectors were obtained with the Pelle cassette in the opposite orientation (Clones 1, 3, 4, and 6).
Figure 4:
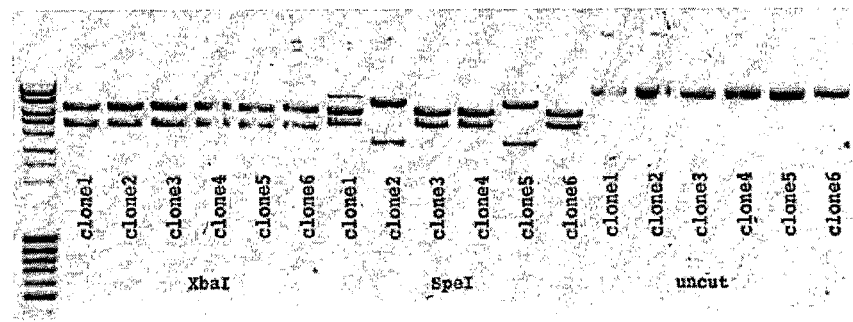

This cloning system saves time compared to traditional cloning systems and generally avoids the need for purifying insert DNA fragments by gel extraction (see FIG. 3), as well as providing a high percentage of recombinant colonies with the recombinant vectors of interest (generally ≧90 and typically up to 100% recombinant clones with the desired insert (FIG. 4). Note that purification of insert DNA fragments provides even higher recombinant frequencies.

Example 2

Pelle-L Vector

Figure 5:
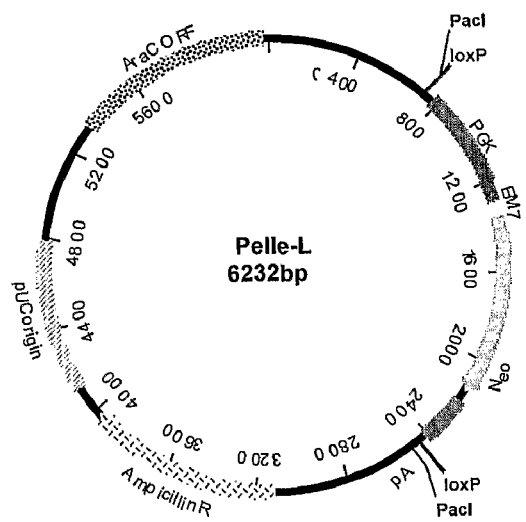
FIG. 5 is a diagrammatic representation of another embodiment of a donor marker plasmid, designated Pelle-L.

FIG. 5 illustrates another embodiment of a Pelle donor plasmid, designated Pelle-L. In this embodiment, the Pelle cassette is flanked by two loxP sites, which permit Cre-mediated excision of the PGK-Neo cassette. PacI can be used to release the Pelle cassette.

Example 3

Pelle-F Vector

Figure 6:
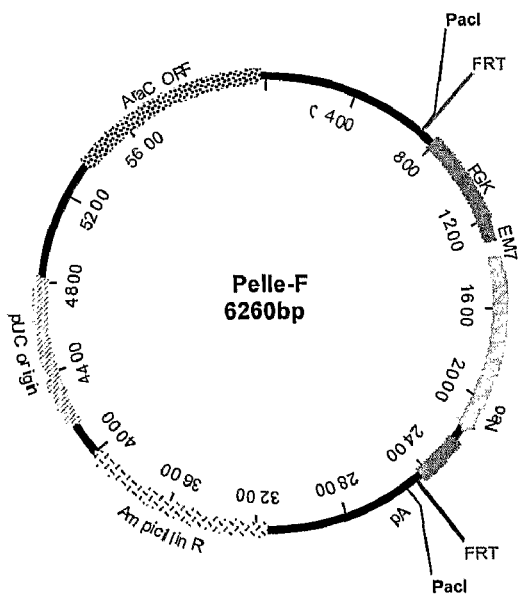
FIG. 6 is a diagrammatic representation of another embodiment of a donor marker plasmid, designated Pelle-F.

FIG. 6 shows yet another embodiment of a Pelle donor plasmid, designated Pelle-F. In this embodiment, the Pelle cassette is flanked by two FRT sites, which permit FLPe-mediated excision of the PGK-Neo cassette. PacI can be used to release the Pelle cassette.

Example 4

Pelle-FK Vector

Figure 7:
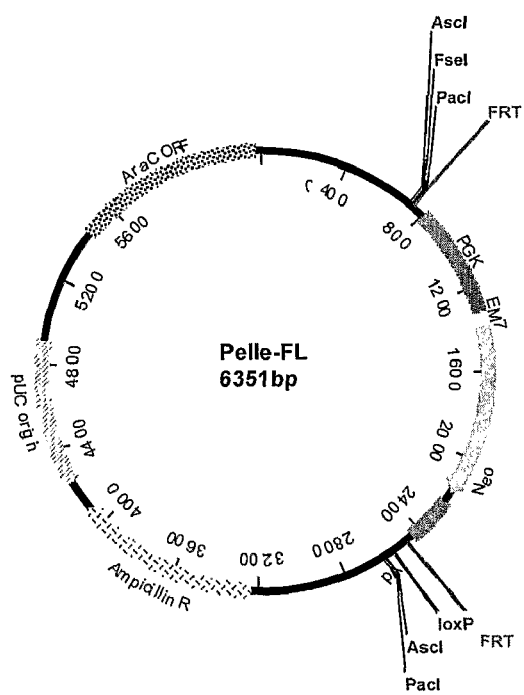
FIG. 7 is a diagrammatic representation of yet another embodiment of a donor marker plasmid, designated Pelle-FL.

FIG. 7 depicts still another embodiment of a Pelle donor plasmid, designated Pelle-FL. In this embodiment, the donor plasmid contains a single loxP site downstream of the polyadenylation signal (pA) and two FRT sites flanking the PGK-Neo cassette. This allows one to construct a conditional gene allele by inserting a loxP site on the 5' end of a target exon. PacI or AscI can be used to excise the Pelle cassette Example 5

Pa1L Vector

Figure 8:
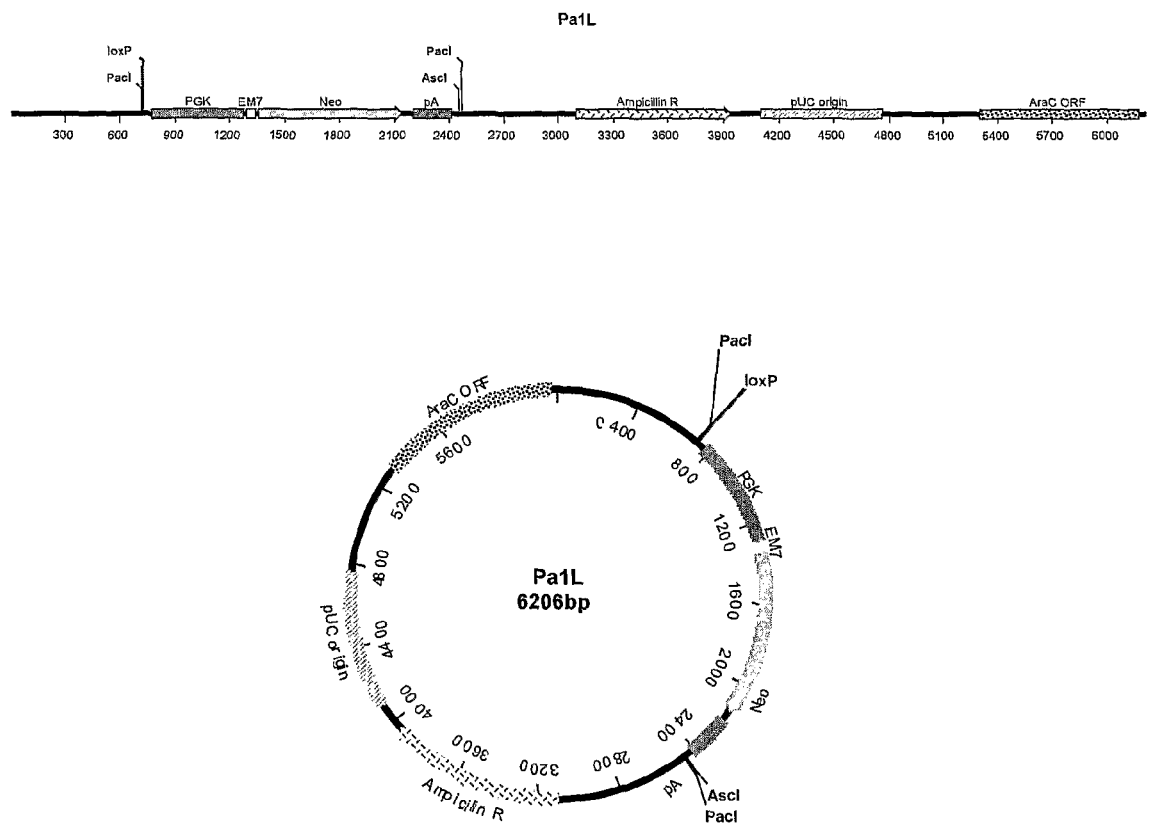
FIG. 8 is a diagrammatic representation of still another embodiment of a donor marker plasmid, designated Pa1L.

FIG. 8 depicts another embodiment of a Pelle donor plasmid, designated Pa1L. This vector contains a single loxP site upstream of the PGK neo cassette and can be used as a secondary construct for double targeting. PacI can be used to release the Pelle cassette.

Example 6

NotINeo Vector

Figure 9:
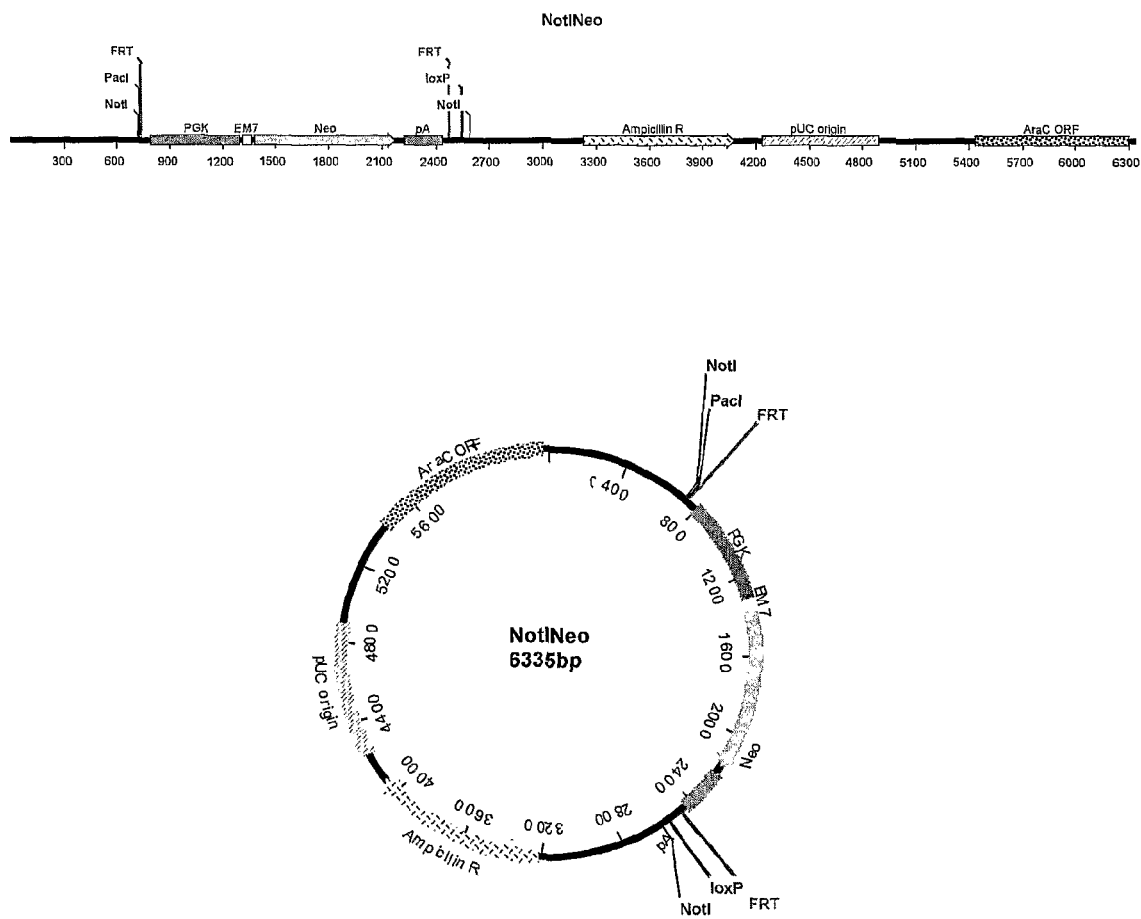
FIG. 9 is a diagrammatic representation of another embodiment of a donor marker plasmid, designated NotINeo.

FIG. 9 shows yet another embodiment of a Pelle donor plasmid, designated NotINeo. This vector contains a single loxP site downstream of the pA signal and two FRT sites flanking the PGK-Neo cassette, which permits the constructions of a conditional gene allele by inserting a loxP site on the 5' end of a target exon. NotI can be used to release the Pelle cassette.

Example 7

FEcoRINeo Vector

Figure 10:
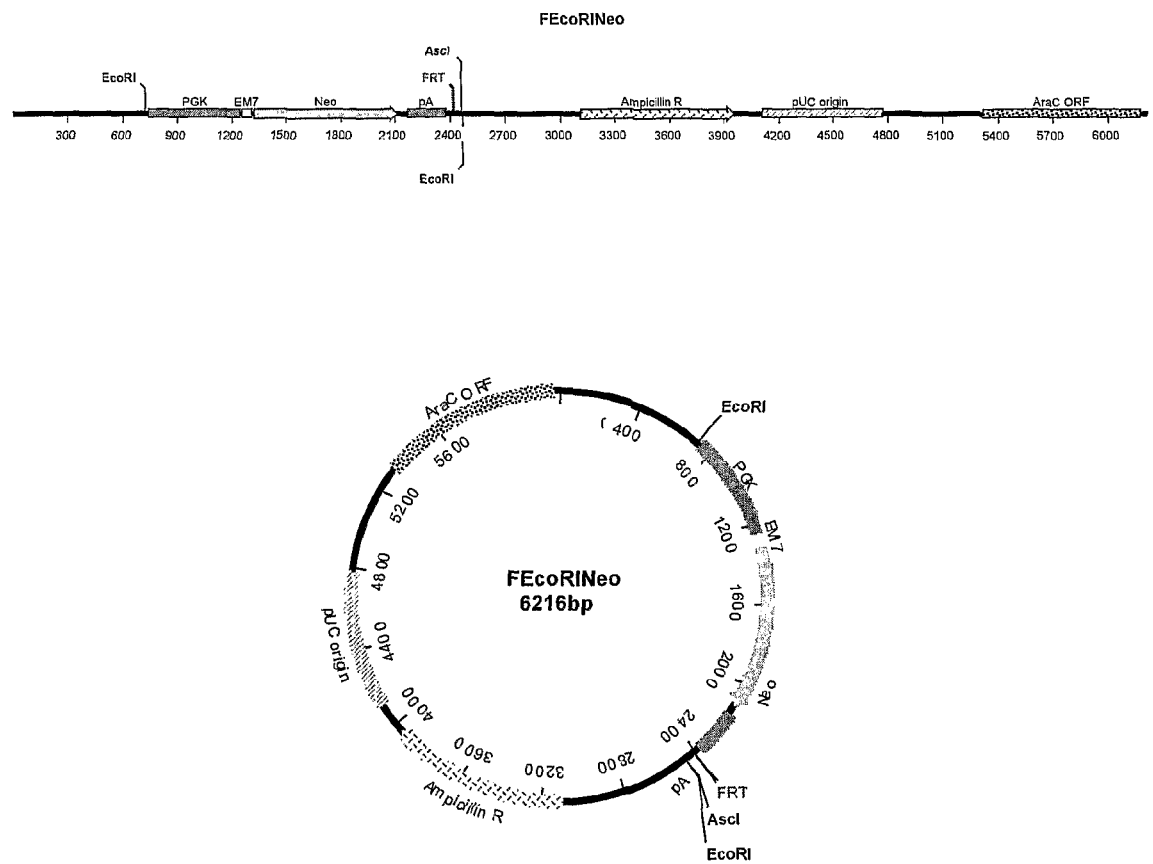
FIG. 10 is a diagrammatic representation of still another embodiment of a donor marker plasmid, designated FEcoRI-Neo.

FIG. 10 depicts still another embodiment of a Pelle donor plasmid, designated FEcoRINeo. This vector contains a single FRT site downstream of the pA signal, which can be used as a secondary construct for double targeting. EcoRI can be used to release the Pelle cassette.

Example 8

LEcoRINeo Vector

Figure 11:
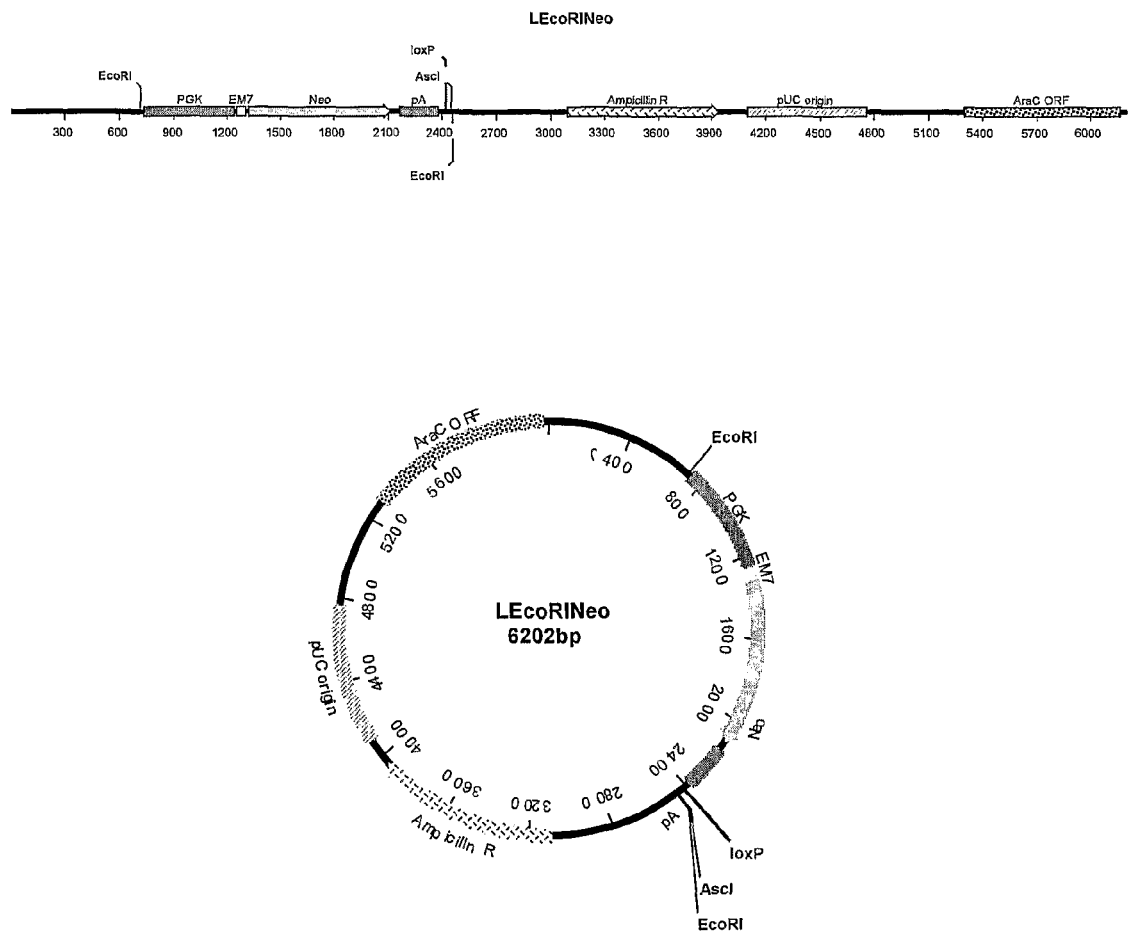
FIG. 11 is a diagrammatic representation of another embodiment of a donor marker plasmid, designated LEcoRI-Neo.

FIG. 11 illustrates another embodiment of a Pelle donor plasmid, designated LEcoRINeo, which contains a single loxP site downstream of the pA signal. This vector can be used as a secondary construct for double targeting. EcoRI can be used to release the Pelle cassette.

Example 9

SgfINeo Vector

Figure 12:
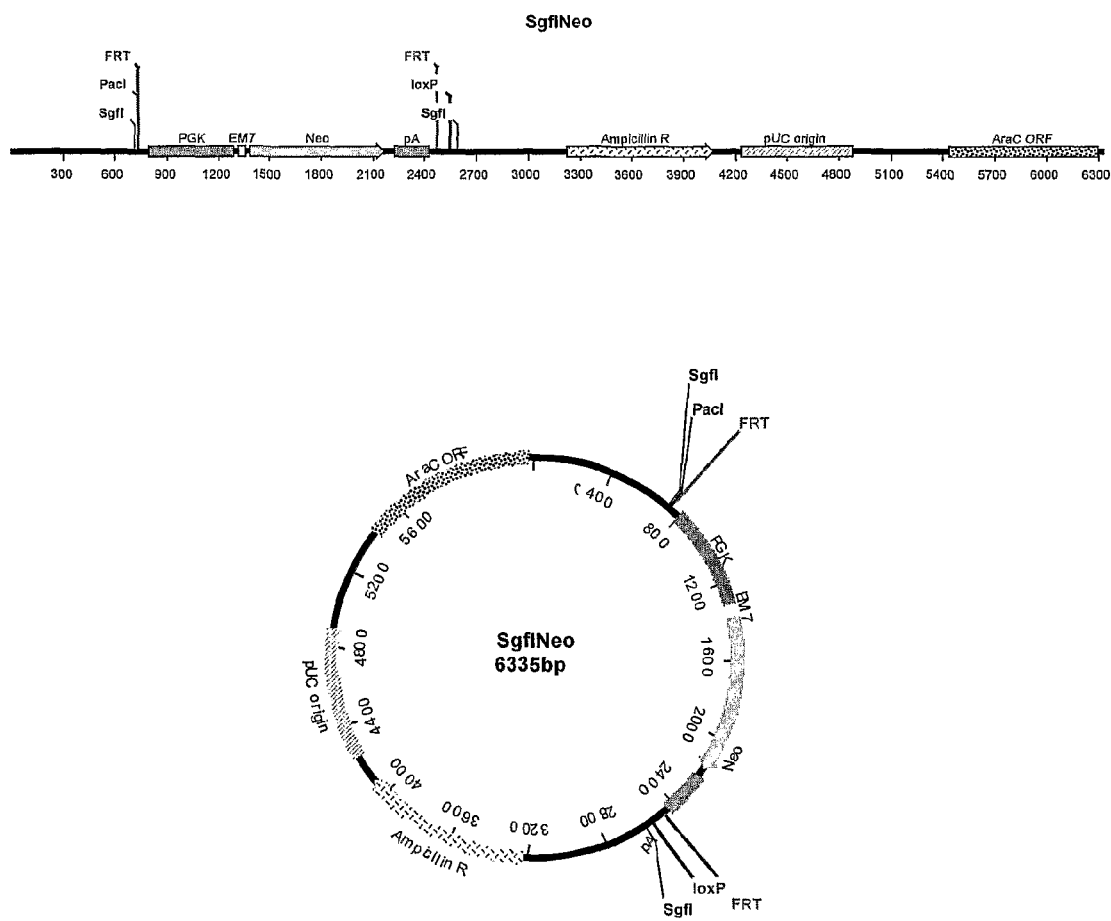
FIG. 12 is a diagrammatic representation of still another embodiment of a donor marker plasmid, designated SgfINeo.

FIG. 12 shows yet another embodiment of a Pelle donor plasmid, designated SgfINeo. This vector contains a single loxP site downstream of the pA signal and two FRT sites flanking the PGK-Neo cassette and allows the construction of a conditional gene allele by inserting a loxP site on the 5' end of your target exon. SgfI can be used to release the Pelle cassette.

Example 10

FAscINeo Vector

Figure 13:
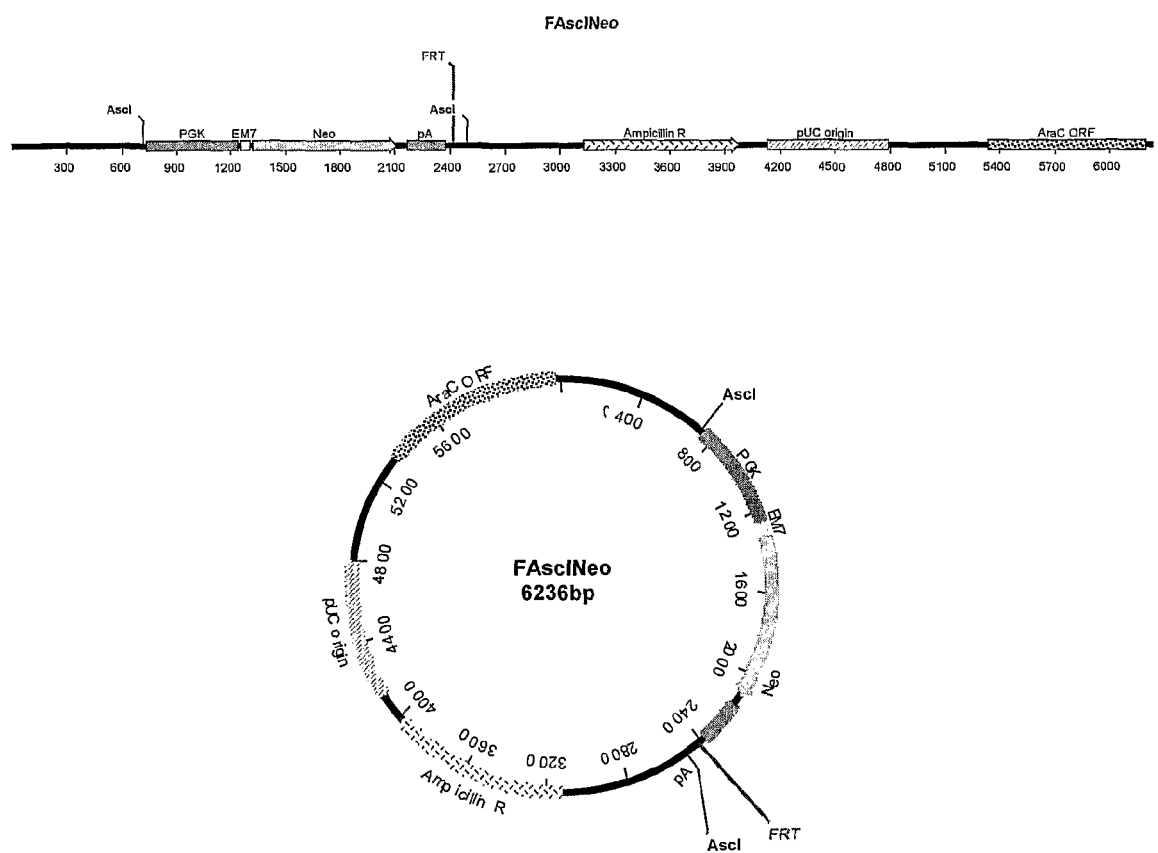
FIG. 13 is a diagrammatic representation of another embodiment of a donor marker plasmid, designated FAscI-Neo.

FIG. 13 shows yet another embodiment of a Pelle donor plasmid, designated FAscINeo. It contains a single FRT site downstream of the pA signal and can be used as a secondary construct for double targeting. AscI can be used to release the Pelle cassette.

Example 11

FNheINeo Vector

Figure 14:
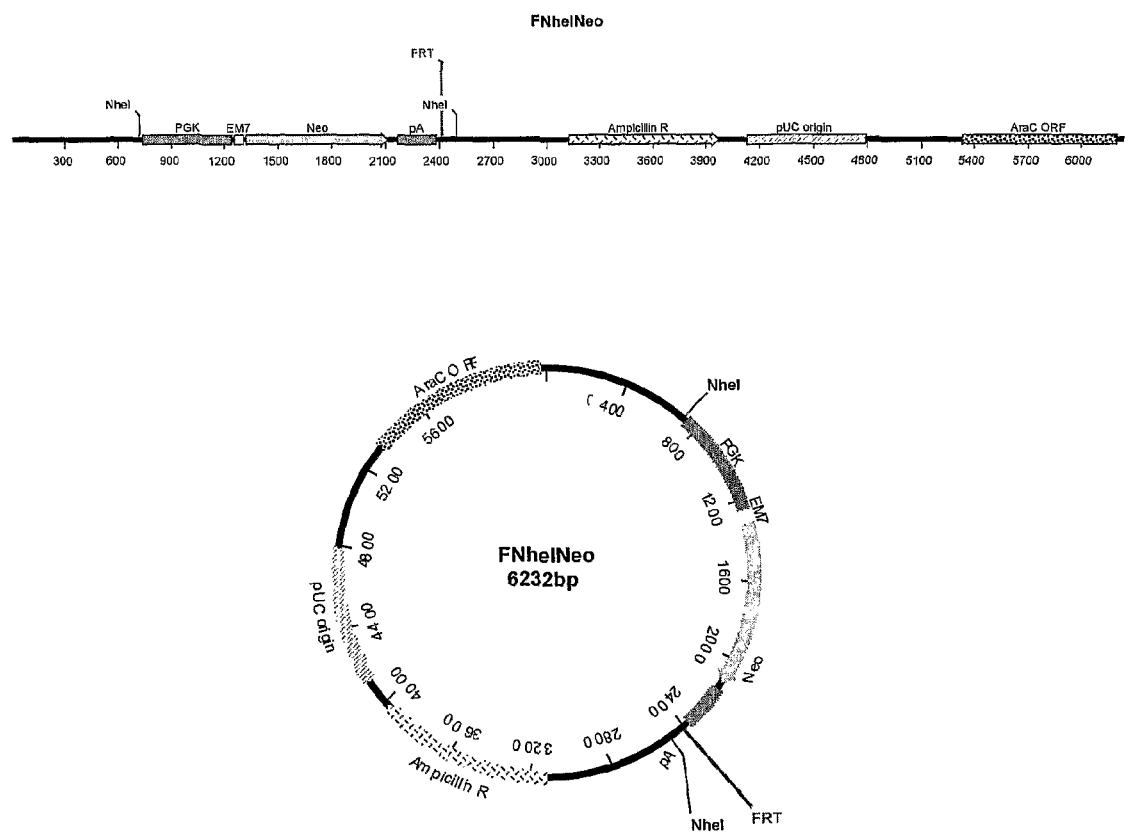
FIG. 14 is a diagrammatic representation of still another embodiment of a donor marker plasmid, designated FNheI-Neo.

FIG. 14 depicts another embodiment of a Pelle donor plasmid, designated FNheINeo, which contains a single FRT site downstream of the pA signal. This vector can be used as a secondary construct for double targeting. NheI can be used to release the Pelle cassette.

Example 12

FBsrGINeo VECTOR

Figure 15:
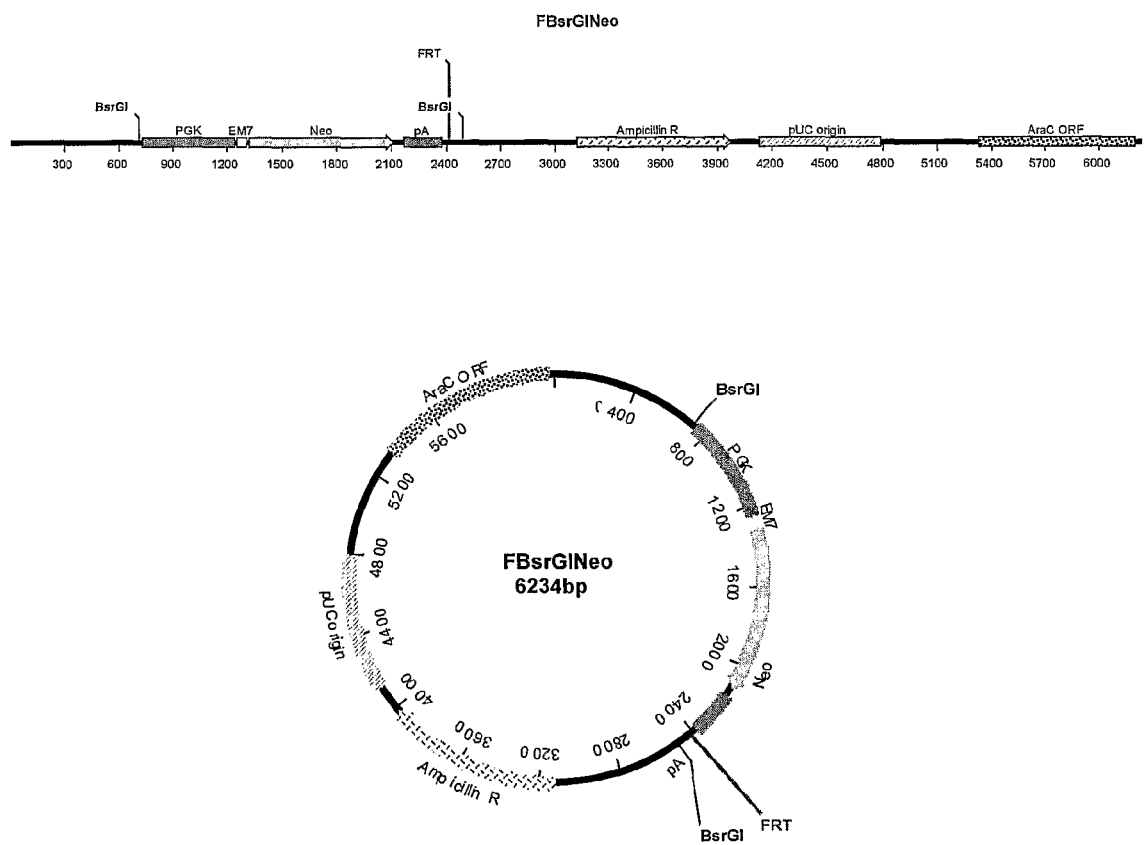
FIG. 15 is a diagrammatic representation of another embodiment of a donor marker plasmid, designated FBsrGINeo.

FIG. 15 illustrates still another embodiment of a Pelle donor plasmid, designated FBsrGINeo, which contains a single FRT site downstream of the pA signal. This vector can be used as a secondary construct for double targeting. BsrGI can be used to excise the Pelle cassette.

Example 13

FBstBINeo Vector

Figure 16:
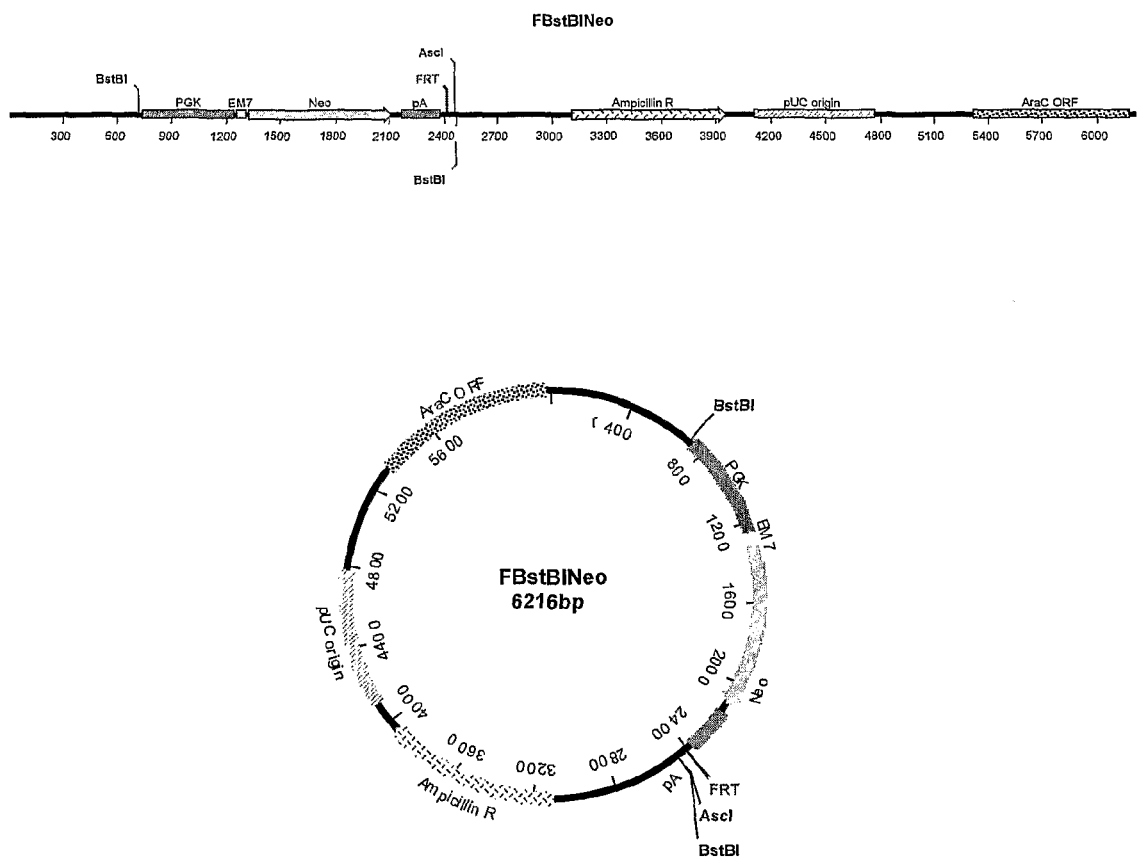
FIG. 16 is a diagrammatic representation of still another embodiment of a donor marker plasmid, designated FBstBI-Neo.

FIG. 16 shows another embodiment of a Pelle donor plasmid, designated FBstBINeo, which contains a single FRT site downstream of the pA signal. This vector can be used as a secondary construct for double targeting. BstBI can be used to release the Pelle cassette.

Example 14

Cloning of a Targeting Construct Consisting of 5 Different Sequences

An illustrative cloning strategy for cloning five different nucleotides sequences, designated sequence 1, sequence 2, sequence 3, sequence 4 and sequence 5, in accordance with the present invention comprises the following steps:

Step 1

Figure 17:
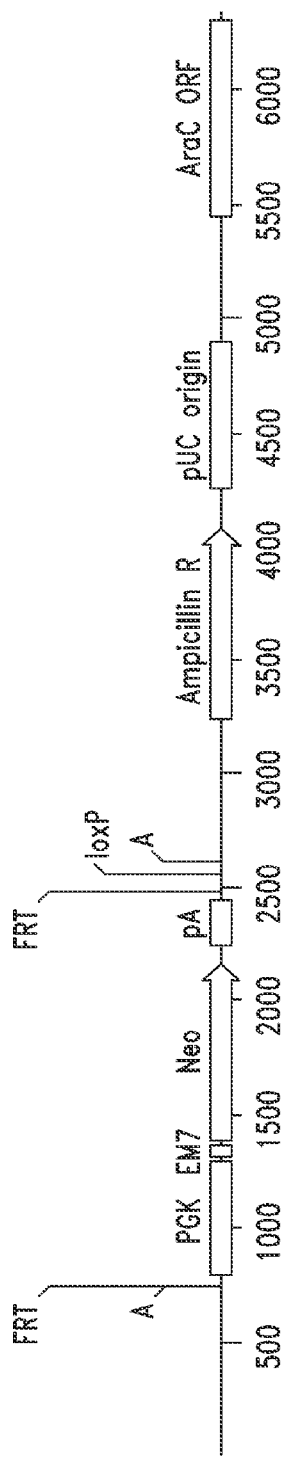
FIG. 17 is diagrammatic representation of a selection cassette flanked by restriction enzyme sites "A".
Figure 18:
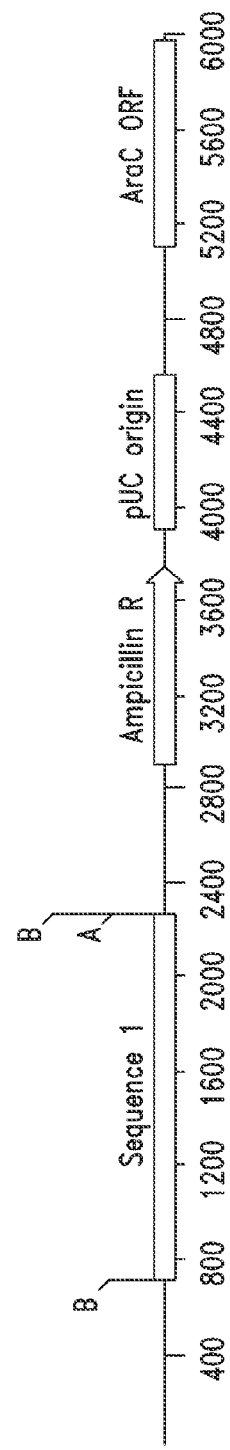
FIG. 18 is a diagrammatic representation of a construct having sequence 1 flanked by restriction enzyme sites "B" and one "A".

The selection cassette flanked by restriction enzyme sites "A" is illustrated in FIG. 17.
Sequence 1 flanked by restriction enzyme sites "B" and one "A" is illustrated in FIG. 18.
Given these two sequences, the selection cassette can be cloned into sequence 1 using the restriction enzyme "A".

Step 2

Figure 19:
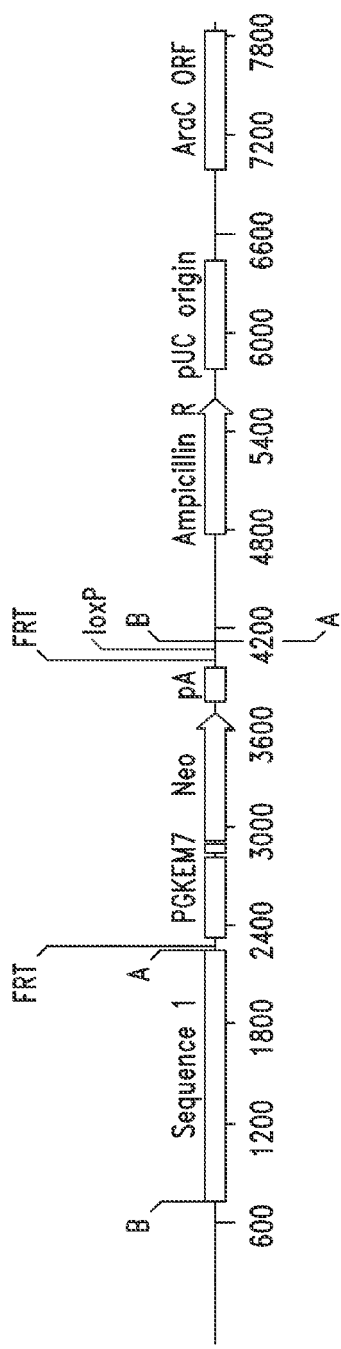
FIG. 19 is a diagrammatic representation of a selection cassette that flanked by restriction enzyme sites "B".
Figure 20:
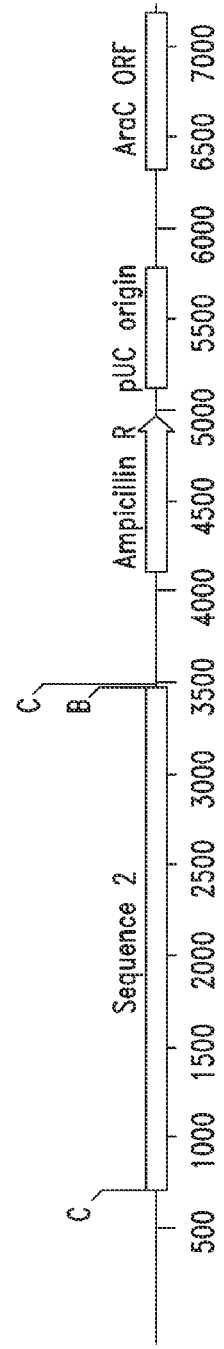
FIG. 20 is a diagrammatic representation of a construct having sequence 2 flanked by restriction enzyme sites "C" and one "B".

The sequence obtained in step 1 becomes the new selection cassette for step 2. The new selection cassette flanked by restriction enzyme sites "B" is illustrated in FIG. 19.
Sequence 2 flanked by restriction enzyme sites "C" and one "B" is illustrated in FIG. 20.
Given these two sequences, the new selection cassette can be cloned into sequence 2 using the restriction enzyme "B".

Step 3

Figure 21:
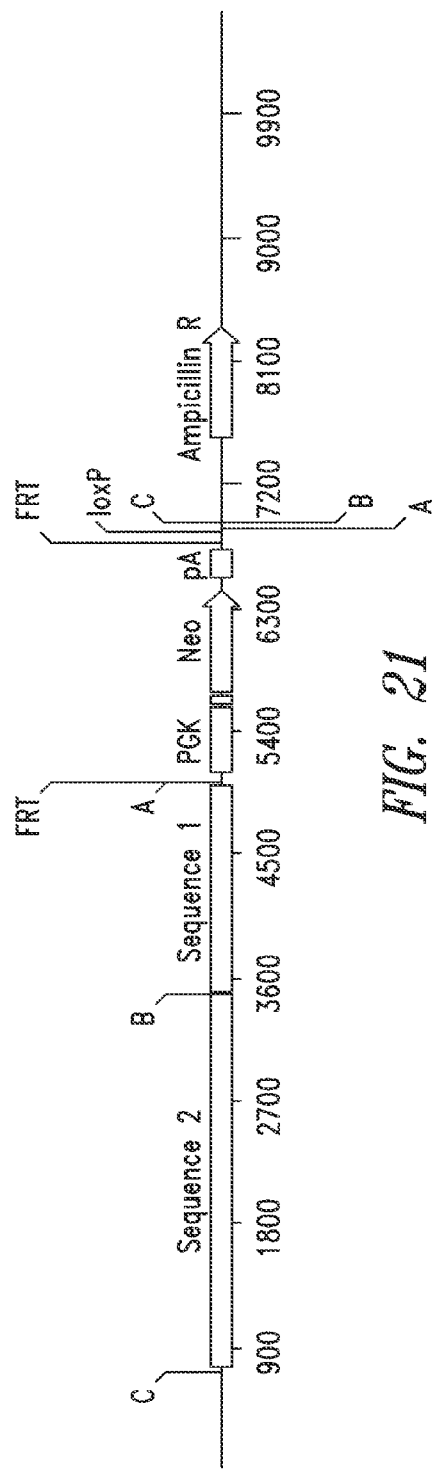
FIG. 21 is a diagrammatic representation of a selection cassette flanked by restriction enzyme sites "C".
Figure 22:
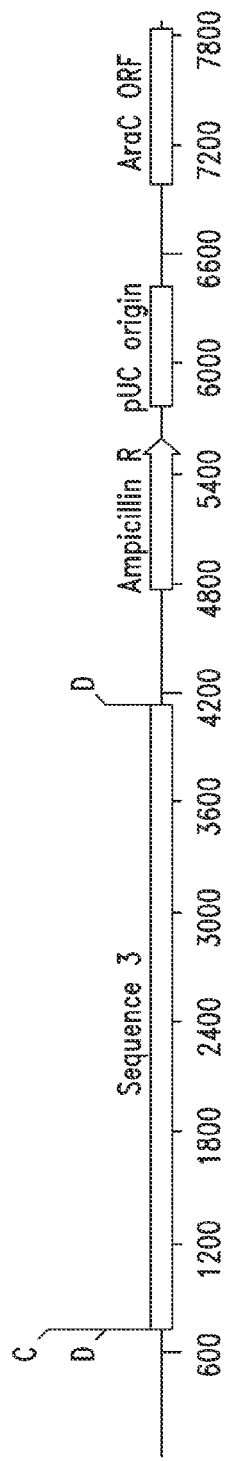
FIG. 22 is a diagrammatic representation of a construct having sequence 3 flanked by restriction enzyme sites "D" and one "C".

The sequence obtained in step 2 becomes the new selection cassette for step 3. The new selection cassette flanked by restriction enzyme sites "C" is illustrated in FIG. 21.
Sequence 3 flanked by restriction enzyme sites "D" and one "C" is illustrated in FIG. 22.
Given these two sequences, the new selection cassette can be cloned into sequence 3 using the restriction enzyme "C".

Step 4

Figures 23, 24:
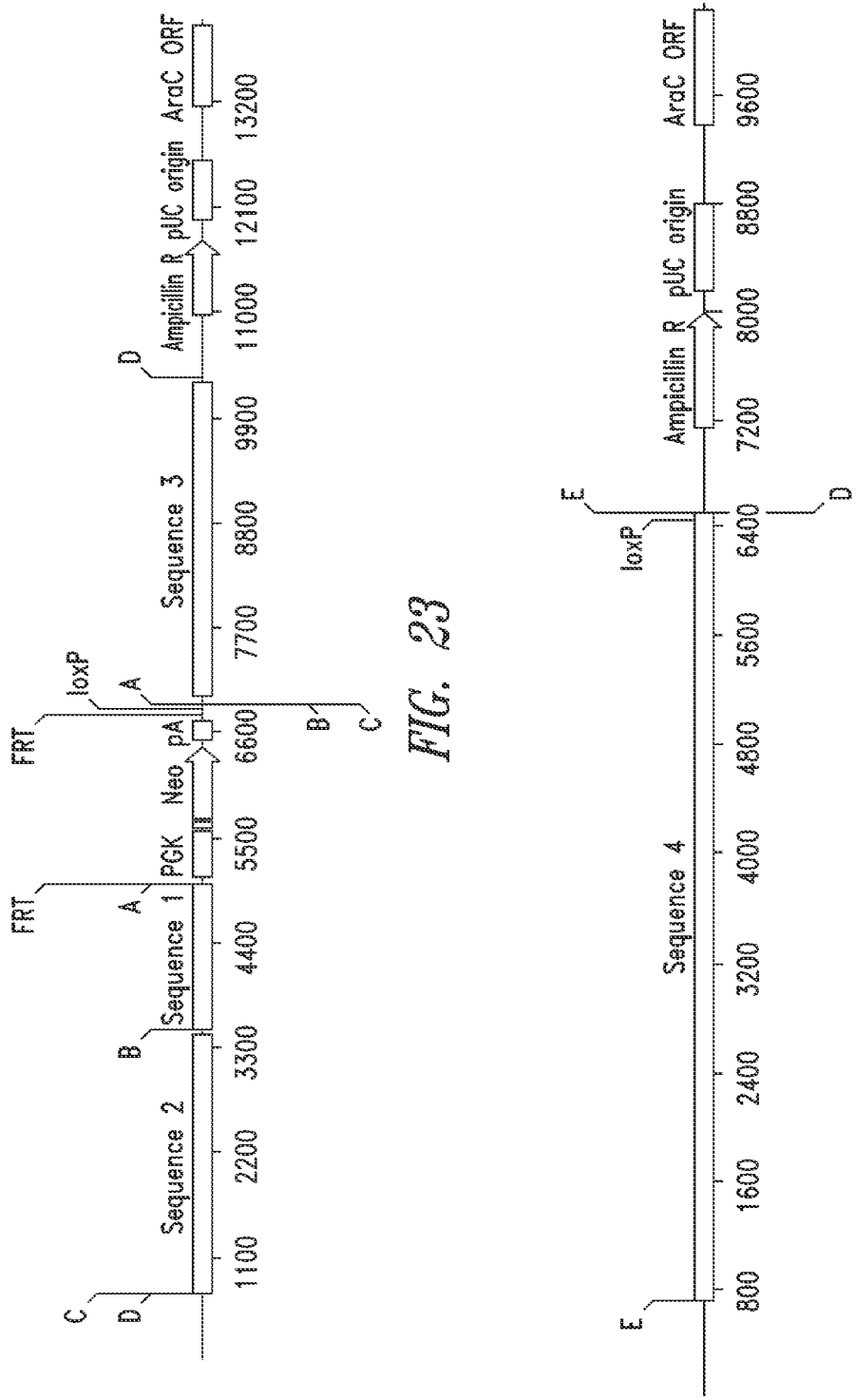
FIG. 23 is a diagrammatic representation of a selection cassette flanked by restriction enzyme sites "D".
FIG. 24 is a diagrammatic representation of a construct having sequence 4 flanked by restriction enzyme sites "E" and one "D".

The sequence obtained in step 3 becomes the new selection cassette for step 4. The new selection cassette flanked by restriction enzyme sites "D" is illustrated in FIG. 23.
Sequence 4 flanked by restriction enzyme sites "E" and one "D" is illustrated in FIG. 24.
Given these two sequences, the new selection cassette can be cloned into sequence 4 using the restriction enzyme "D".

Step 5

Figure 25:
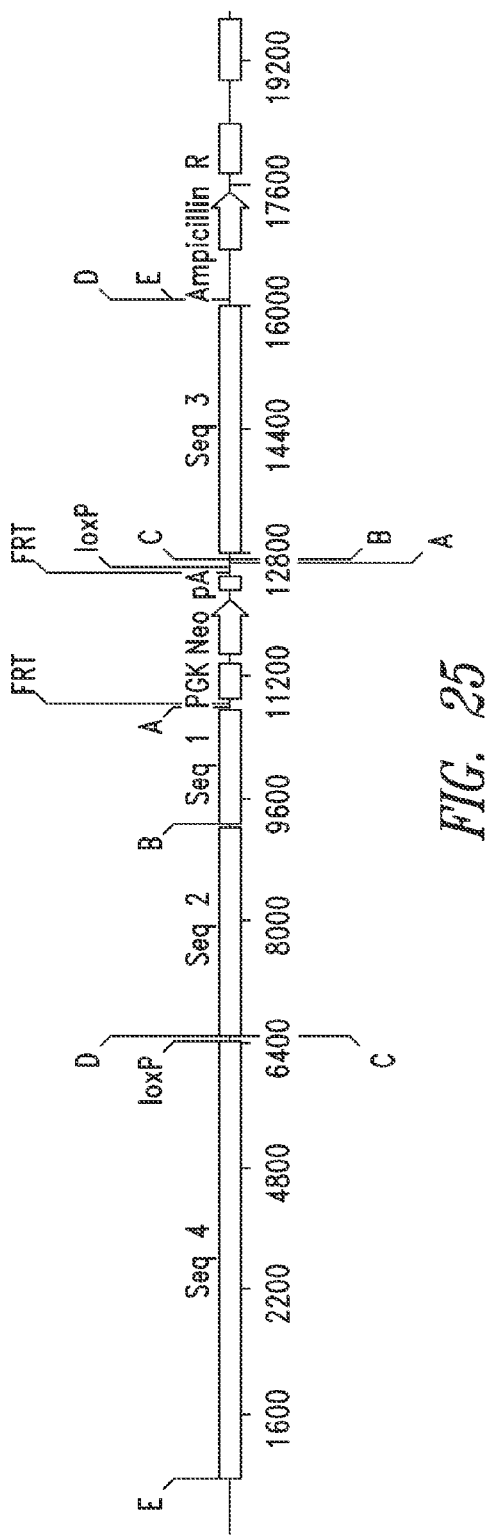
FIG. 25 is a diagrammatic representation of a selection cassette flanked by restriction enzyme sites "E".
Figure 26:
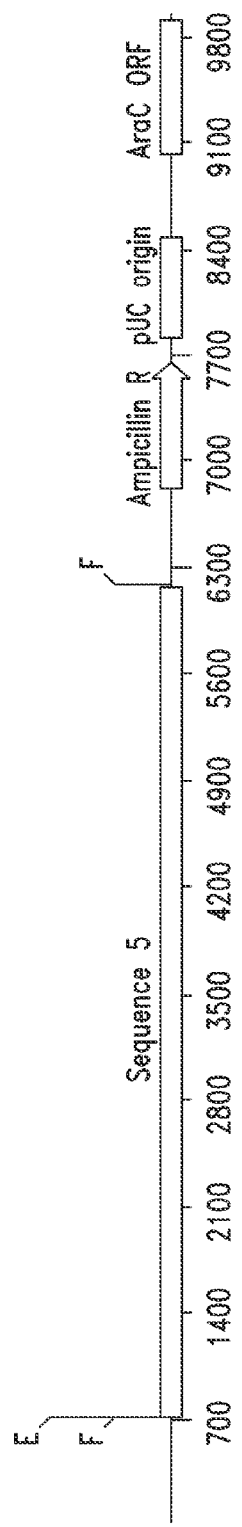
FIG. 26 is a diagrammatic representation of a construct having sequence 5 flanked by restriction enzyme sites "F" and one "E".
Figure 27:
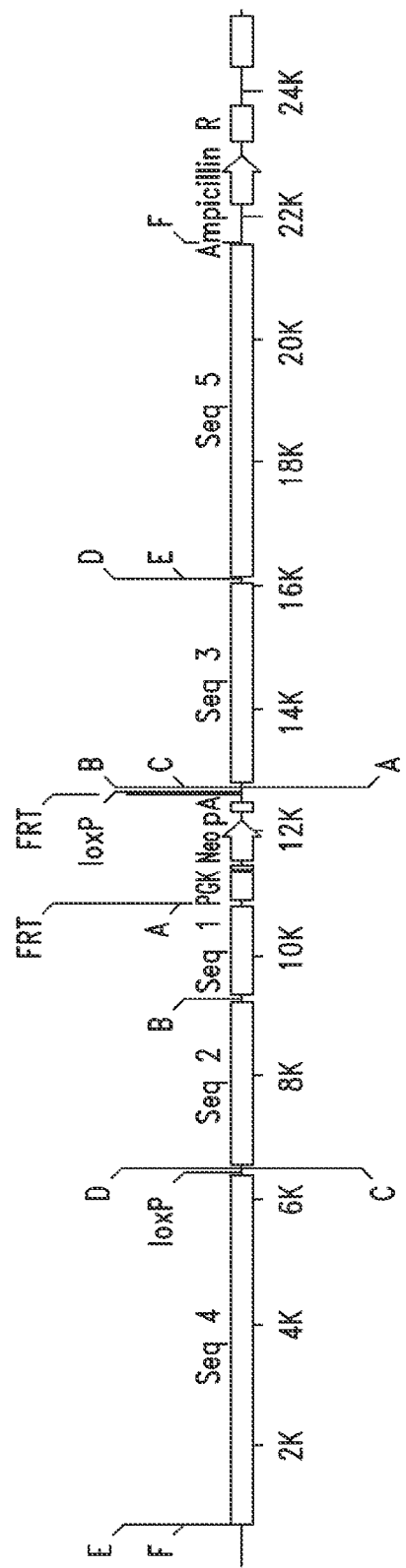
FIG. 27 is a diagrammatic representation of a targeting construct containing 5 different sequences, sequence 1, sequence 2, sequence 3, sequence 4, and sequence 5.

The sequence obtained in step 4 becomes the new selection cassette for step 5. The new selection cassette flanked by restriction enzyme sites "E" is illustrated in FIG. 25.
Sequence 5 flanked by restriction enzyme sites "F" and one "E" is illustrated in FIG. 26.
Given these two sequences, the new selection cassette can be cloned into sequence 5 using the restriction enzyme "E".
The Final targeting construct obtained after step 5 will be as illustrated in FIG. 27.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 720131_401USPC_SEQUENCE_LISTING.txt. The text file is 1 KB, was created on Jun. 9, 2008, and is being submitted electronically via EFS-Web.

(b) introducing the first recombinant construct into a first set of host cells;
(c) screening for the first set of host cells with the first identifiable characteristic to thereby identify a first set of recombinant cells that contain the first recombinant construct;
(d) obtaining the first cassette from the first recombinant construct corresponding to the first set of recombinant cells;
(e) inserting the first cassette into the second recipient construct that
   (i) lacks the first marker sequence, but
   (ii) comprises a second heterologous nucleic acid sequence
to form a second recombinant construct comprising a second cassette that
   (i) is optionally portable into a third recipient construct,
   (ii) lacks an origin of replication, and
   (iii) comprises the first cassette and the second heterologous nucleic acid sequence;
(f) introducing the second recombinant construct into a second set of host cells, and

What is claimed is:

1. A method for sequentially cloning a plurality of heterologous nucleic acid sequences, comprising:
   (a) inserting a portable segment that
      (i) lacks an origin of replication, but
      (ii) comprises a first marker sequence that confers a first identifiable characteristic on host cells that contain the first marker sequence,
   into a first recipient construct that
      (i) lacks the first marker sequence, but
      (ii) comprises a first heterologous nucleic acid sequence
   to thereby form a first recombinant construct that comprises a first cassette that
      (i) is portable into a second recipient construct,
      (ii) lacks an origin of replication, and
      (iii) comprises the first marker sequence and the first heterologous nucleic acid sequence;

(g) screening for the second set of hosts cells with the first identifiable characteristic to thereby identify a second set of recombinant cells that contain the second recombinant construct.

2. The method according to claim 1, further comprising: (h) obtaining the second cassette from the second recombinant construct corresponding to the second set of recombinant cells.

3. The method according to claim 2, further comprising repeating steps (e) to (g) and optionally (h) at least once to assemble a chimeric construct of interest.

4. The method according to claim 2, further comprising repeating steps (e) to (g) and optionally (h) multiple times to assemble a chimeric construct of interest.

5. The method according to claim 1, further Comprising:
identifying the first set of recombinant host cells that display, in addition to the first identifiable characteristic, a second identifiable characteristic that is conferred by a second marker sequence that resides in the first recipient construct, or identifying the second set of recombinant host cells that display, in addition to the second identifiable characteristic, a second identifiable characteristic that is conferred by a second marker sequence that resides in the second recipient construct, wherein the second marker sequence is different from the first marker sequence.

6. The method according to claim 5, wherein the first and second marker sequences are selected from sequences of selectable markers and screenable markers.

7. The method according to claim 1, wherein the first and second recipient constructs are selected from vectors and nucleic acid sequences residing in the genome of the first and second sets of host cells.

8. The method according to claim 1, wherein
(A) the first cassette that is introduced into the second recipient construct is provided with a second marker sequence that confers a second identifiable characteristic that is different from the first identifiable characteristic conferred by the first marker sequence, or
(B) the second cassette is introduced into the third recipient construct, and is provided with a second marker sequence that confers a second identifiable characteristic that is different from the first identifiable characteristic conferred by the first marker sequence.

9. The method according to claim 3, further comprising excising at least a portion of the first marker sequence after assembly of the chimeric construct of interest.

10. The method according to claim 9, wherein the first marker sequence is excised, in whole or in part, using a recombinase protein that recognizes target sites located within or adjacent to the first marker sequence to thereby mediate the excision.

11. The method according to claim 1, wherein the first and second heterologous nucleic acid sequences are selected from: (1) a nucleic acid sequence that is homologous with a region of a target site in the genome of the first or second set of host cells; (2) a transcriptional regulatory element; (3) a translational regulatory element; (4) a sequence that comprises at least one restriction enzyme site; (5) a marker sequence; (6) a sequence that encodes a RNA molecule; (7) a sequence that encodes a polypeptide; (8) a recombination site; and (9) an antisense molecule.

12. The method according to claim 1, wherein
(A) the first cassette is a first targeting cassette for site-specific homologous recombination at a first target site in the first recipient construct or in the genome of the first set of host cells, wherein the first set of host cells are capable of undergoing homologous recombination, or
(B) the second cassette is a second targeting cassette for site-specific homologous recombination at a second target site in the second recipient construct or in the genome of the second set of host cells, wherein the second set of host cells are capable of undergoing homologous recombination.

13. The method according to claim 1, wherein
(A) the first cassette is amplified by nucleic acid amplification from the first recombinant construct and inserted into the second recipient construct, or
(B) the second cassette is amplified by nucleic acid amplification from the second recombinant construct and optionally inserted into the third recipient construct.

14. The method according to claim 13, wherein
(A) the nucleic acid amplification of the first cassette employs at least one primer that comprises
(1) a first nucleotide sequence that is complementary to a terminal portion of the first cassette, and
(2) a first site that serves to insert one end of the amplified first cassette into the second recipient construct, or
(B) the nucleic acid amplification of the second cassette employs at least one primer that comprises
(1) a second nucleotide sequence that is complementary to a terminal portion of the second cassette, and
(2) a second site that serves to insert one end of the amplified second cassette into the third recipient construct.

15. The method according to claim 14, wherein the first or second site is cleavable by a restriction enzyme.

16. The method according to claim 1, wherein
(A) the first cassette is physically transferred from the first recombinant construct to the second recipient construct, or
(B) the second cassette is physically transferred from the second recombinant construct to the third recipient construct.

17. The method according to claim 16, wherein the physical transfer comprises excision of the cassette from the donor construct using, a restriction endonuclease, sonication, shearing or recombination.

* * * * *